United States Patent [19]
Mosbach et al.

[11] Patent Number: 6,127,154
[45] Date of Patent: *Oct. 3, 2000

[54] METHODS FOR DIRECT SYNTHESIS OF COMPOUNDS HAVING COMPLEMENTARY STRUCTURE TO A DESIRED MOLECULAR ENTITY AND USE THEREOF

[76] Inventors: Klaus Mosbach, Lackalaenga 31, Furulund 24402, Sweden; Peter A. G. Cormack, 56 Lartside Street, Flat 2/L, Langside, Glasgow G429TG, United Kingdom; Olof Ramström, 59. Chemin du Beulenworth, F-67000 Strasbourg, Sweden; Karsten Haupt, 7 Rue de l'Atlas, 75019 Paris, France

[ * ] Notice: This patent is subject to a terminal disclaimer.

[21] Appl. No.: 09/303,656

[22] Filed: May 3, 1999

Related U.S. Application Data

[62] Division of application No. 09/145,267, Sep. 2, 1998, which is a continuation-in-part of application No. 08/626,342, filed as application No. PCT/SE95/00135, Feb. 10, 1994.

[30] Foreign Application Priority Data

Feb. 10, 1994 [SE]  Sweden .................................. 9400450

[51] Int. Cl.[7] .................................. C08J 5/00; C08J 9/26; C08J 9/28

[52] U.S. Cl. ..................................... 435/173.1; 530/387.1; 530/388.1; 530/388.9; 530/389.8; 427/487; 436/501; 436/85; 210/660; 210/666; 210/670; 210/679; 210/692; 210/767

[58] Field of Search ..................................... 264/108, 219, 264/220, 221, 225, 226, 227, 330, DIG. 44, 330.11, 331.11, 331.16, 331.19; 424/78.08, 78.37; 526/238.1, 238.2; 435/173.1, 173.2, 173.4, 183, 188.5; 530/387.1, 388.1, 388.9, 389.8

[56] References Cited

U.S. PATENT DOCUMENTS

| | | | |
|---|---|---|---|
| 4,447,374 | 5/1984 | Tanaka | 264/483 |
| 5,110,833 | 5/1992 | Mosbach | 521/50 |
| 5,630,978 | 5/1997 | Domb | 264/330 |

OTHER PUBLICATIONS

"Insulin's Structure as a Modified and Monomeric Molecule", Ru Chang Bi et al., *Biopolymers,* vol. 23, pp. 391–395 (1984).

"Structure and Stability of Insulin Dissolved in 1–Octanol", James Matsuura et al., *J. Am. Chem. Soc.,* 1993, vol. 115, pp. 1261–1264.

The Emerging Technique of Molecular Imprinting and Its Future Impact on Biotechnology, *Biotechnology,* vol. 14, pp. 163–170 (1996).

*Primary Examiner*—Frederick Krass
*Attorney, Agent, or Firm*—Burns, Doane, Swecker & Mathis, L.L.P.

[57] ABSTRACT

Compounds which possess a complementary structure to a desired molecule, such as a biomolecule, in particular polymeric or oligomeric compounds, which are useful as in vivo or in vitro diagnostic and therapeutic agents are provided. Also, various methods for producing such compounds are provided. These polymeric or oligomeric compounds are useful in particular as antimicrobial agents, receptor, hormone or enzyme agonists and antagonists.

38 Claims, 12 Drawing Sheets

FIG. 6
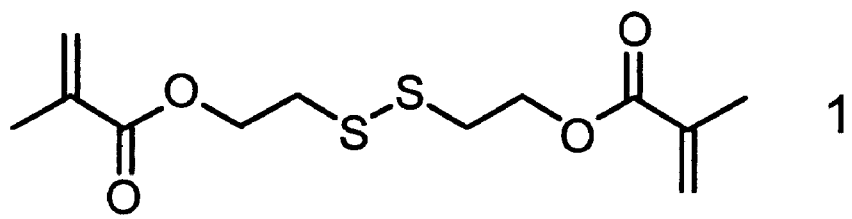 1
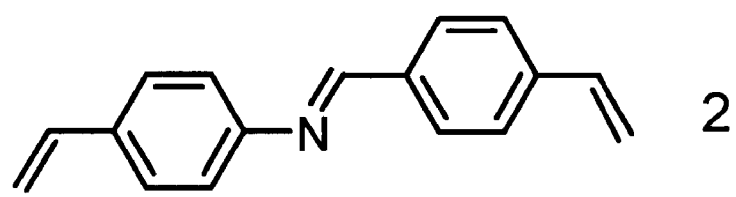 2
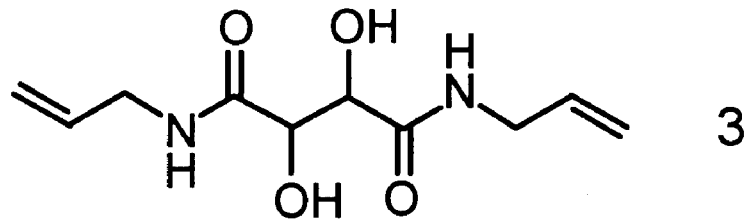 3
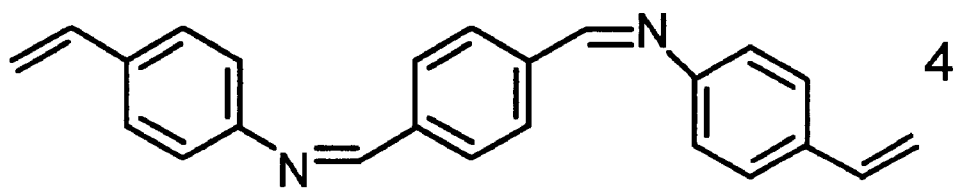 4
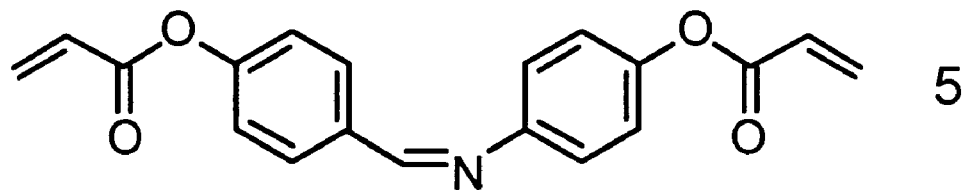 5

FIG. 9
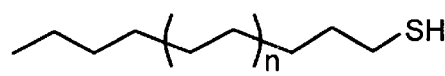
1
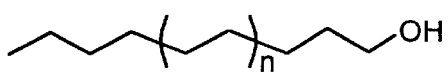
2
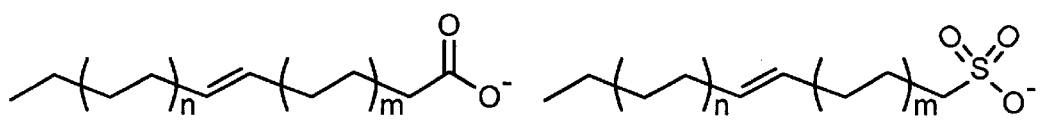
3
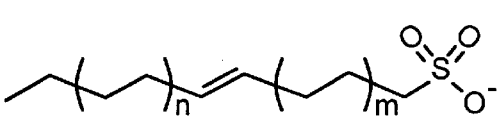
4
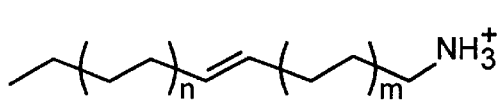
5
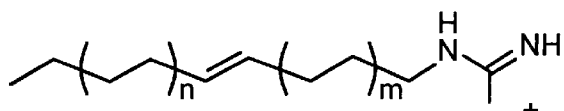
6
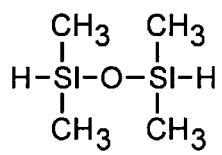
7

FIG. 10
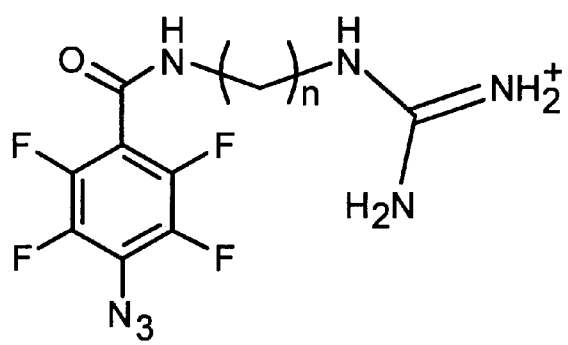
1
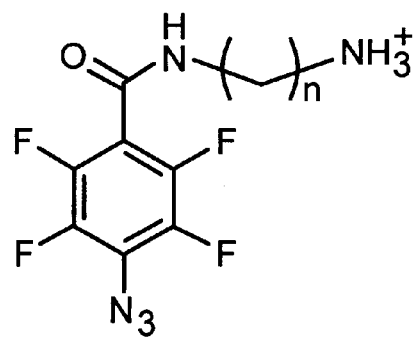
2
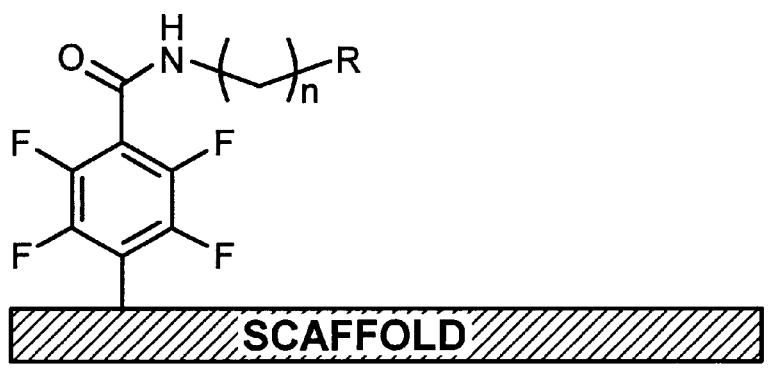
3

METHODS FOR DIRECT SYNTHESIS OF COMPOUNDS HAVING COMPLEMENTARY STRUCTURE TO A DESIRED MOLECULAR ENTITY AND USE THEREOF

RELATED APPLICATIONS

This application is a divisional of application Ser. No. 09/145,267, filed Sep. 2, 1998; in turn, which is a continuation-in-part of application Ser. No. 08/626,342, filed Apr. 2, 1996; in turn, which is a 371 of Application No. PCT/SE95/00135, filed Feb. 10, 1994.

BACKGROUND OF THE INVENTION

1. Field of the Invention

The present invention pertains to methods for the direct synthesis of compounds, e.g., polymeric or oligomeric compounds, that possess a complementary structure to a desired template molecule, e.g., a compound having biological activity. The present invention further pertains to compounds, e.g., polymers or oligomers produced by such methods, and the use thereof, e.g., as therapeutics or diagnostics based on their complementary structure to a molecule having a known activity. The direct synthesis methods provided herein, which are an extension of the technique generally known as "molecular imprinting," provide a powerful means of producing a compound having a desired activity. While the technique should be applicable for the synthesis of a complementary binding molecule to any desired compound, the most significant application comprises direct drug synthesis. As discussed in detail infra, the subject invention is particularly useful for direct synthesis of agonists or antagonists for desired molecules, e.g., enzymes, hormones, receptors and other proteins; molecules that affect gene expression, molecules that affect the binding of biomolecules; e.g., cells or cell-like moieties to other ligands; and the synthesis of improved diagnostic agents.

2. Description of the Prior Art

In traditional drug screening methods, natural products are generally isolated, e.g., from plant, animal or microbial extracts and tested for biological activity. These methods generally entail complex purification and characterization procedures, and the eventual identification of a natural product having biological activity, e.g., an antimicrobial agent. These natural products are used in their native form, or more typically they are improved by the synthesis of synthetic analogs thereof. These synthetic analogs are then tested for biological activity and the most active compounds become the "drug leads." These compounds are then used to develop the next generation of synthetic analogs.

While these methods have resulted in useful drugs, both natural and synthetic variants, they are generally very inefficient. Typically, testing must be carried out in animals, or potentially in vitro if there is a suitable in vitro model to test activity. This is problematic as many assays, in particular animal testing, require large quantities of compound. This is disadvantageous as it limits the number of compounds which can be feasibly tested.

Also, such methods are inherently complex and unpredictable. Often it is difficult to predict and establish the structure/activity relationship among different compounds tested for activity. This is difficult to assess, especially if the tested compounds vary significantly in structure. This makes it difficult to determine the particular portion of the molecule that is significant for activity. Generally, only by screening large numbers of compounds is this able to be determined.

Also, such methods are prone to error. Often compounds that score positive in in vitro assays, and even animal models, are inactive in humans. Conversely, compounds which score negative in vitro may actually be active but score negative because of solubility problems which enable an otherwise active compound to cross the cell membrane in vivo.

Recently, in an effort to obviate some of the problems and inefficiencies of traditional drug screening and synthesis methods, random screening techniques have been developed to identify active compounds. In such methods, a library, which is simply a collection of different chemical or biological entities, is screened for one or more properties, e.g., binding to a particular ligand. Such libraries include, by way of example, compound libraries, peptide libraries, oligosaccharide libraries, and nucleic acid sequence libraries. Typically, the compounds in a particular library possess a related structure, origin and/or function.

A particular type of library used by many research groups involved in drug design is the "combinatorial library." This simply refers to a library in which the individual members comprise systematic or random combinations of a limited set of basic elements. Randomization may be complete or partial. For example, some positions of the tested compounds may be fixed or varied systematically and others randomly varied. Typically, the members of a combinatorial library constitute oligomers or polymers, which vary based on the particular monomers, the connecting linkages, and/or the length of the oligomer or polymer. Ideally, the members of a combinatorial library are selected such that they can be screened for a particular activity or activities simultaneously. (See Fenniri, "Recent Advances at the Interface of Medicinal and Combinatorial Chemistry. Views on Methodologies for the Generation and Evaluation of Diversity and Application to Molecular Recognition and Catalysis," Curr. Med. Chem., 3:343–378 (1996), for a review of combinatorial library techniques.)

One particular type of combinatorial library is the peptide library. These libraries may comprise peptides made by synthetic methods or by microbial synthesis. In particular, the use of phage or bacterial libraries wherein a phage particulate or bacterium expresses a desired peptide on its surface (by operable linkage of the corresponding DNA to a sequence that encodes a surface protein) are well known. These libraries are advantageous because peptides comprise structures that mimic many biological molecules, i.e., proteins. It is possible by synthetic or biological techniques to generate a large array of different peptides of a particular size and sequence, which are thereupon screened for a particular desired property. Microbial surface display libraries are advantageous in that large numbers of different peptides may be obtained in large quantities relatively efficiently. (See G. P. Smith and V. A. Petrenko, "Phage Display," Chem. Rev., 97:391–410 (1997), for a review on phase display libraries.)

However, these methods also suffer significant disadvantages. In particular, peptides are often costly to synthesize, may be unstable (e.g., in the presence of proteases), and often are unable to cross cellular membranes. Therefore, other molecules, i.e., small organic molecules, still are preferred drug candidates.

Such compounds can also be screened by library screening methods. However, small molecules often are not trivial to synthesize in quantities necessary for screening. This disadvantage has somewhat been alleviated by recent methods which have downsized targets to the molecular level, and the automation of screens which have reduced the amount of compound necessary for assay to small amounts. These enhancements have enabled the utilization of combinatorial chemistry libraries instead of traditional chemical compound libraries. Combinatorial chemistry permits the rapid, relatively inexpensive synthesis of large numbers of compounds in small quantities suitable for automated assays directed at molecular targets. Numerous research groups and companies have reported the design of combinatorial chemistry libraries which exhibit a significant range of structural diversity. (See, e.g., P. M. Doyle, "Combinatorial Chemistry in the discovery and development of drugs," *J. Chem. Tech. Biotech.*, 64(4):317–324 (1995); E. M. Gordon, "Libraries of non-polymeric organic molecules," *Curr. Opin. Biotech.*, 6(6):624–637 (1995)). However, such screening processes still are often ineffective.

Thus, based on the foregoing, methods that provide for the direct synthesis of compounds having a desired activity, e.g., a desired biological activity would be highly desirable. Moreover, compounds generated by such methods would be extremely desirable because of their potential application as drugs and diagnostic agents.

BRIEF SUMMARY OF THE INVENTION

Toward that end, the present inventors have developed a highly efficient means of directly synthesizing a compound, in particular a polymer or oligomer having a desired function, typically a biological activity, that enables such compound to be used as a drug, catalyst, competitive affinity ligand inhibitor, competitor, agonist, antagonist, or diagnostic agent. The present inventors have in particular developed a highly efficient means for the direct synthesis of compounds, e.g., polymers or oligomers, that possess a complementary structure to a desired molecular entity, typically a biomolecule, or portion thereof, e.g., the active site, that are useful, e.g., as agonists or antagonists of enzymes, hormones, receptors, for regulating gene expression, as antimicrobial or antiviral agents, as reaction catalysts, and in general for any activity which relies upon the ability of a compound to bind to another moiety based on its complementary structure.

OBJECTS OF THE INVENTION

It is an object of the invention to solve the problems of previous indirect drug identification methods.

It is a specific object of the invention to directly produce a compound that possesses a complementary structure to any desired molecular entity or a portion thereof, preferably a biomolecule.

It is a more specific object of the invention to directly produce a compound that possesses a complementary structure to a desired molecular entity or a portion thereof, comprising the following:

(i) selecting a desired molecule, typically a biomolecule, to which a compound, e.g., a polymer or oligomer, having a complementary structure is to be obtained;

(ii) contacting such molecule with one or more monomers, optionally in the presence of one or more crosslinking agents, under conditions that allow for such monomers to associate either covalently or non-covalently with specific moieties exposed on the chosen compound;

(iii) optionally adding one or more crosslinking agents, if not already present, and polymerizing the monomers which are associated around the desired compound to produce a compound, i.e., polymer or oligomer, that possesses a complementary structure to specific moieties which are exposed on such compound; and (iv) recovering the resultant compound, i.e., polymer or oligomer, that possesses a complementary structure to the desired molecule by the removal of the compound from the desired molecule.

An even more specific object of the invention is to provide a compound that possesses a complementary structure to a desired molecular entity, e.g., a biomolecule such as a microbial or mammalian cell or portion thereof comprising the following steps:

(i) immobilizing a desired molecule, e.g., a microbial cell to a support, e.g., a thin layer support such as a silicon wafer;

(ii) coating (e.g., by spin-coating) onto such support which includes the immobilized molecule a polymeric coating that can be crosslinked under controlled conditions, e.g., exposure to irradiation;

(iii) selectively crosslinking only those portions of the polymeric coating that coat the immobilized molecule, e.g., by use of irradiation and a photomask to protect other areas of the polymer coating contained on the support;

(iv) removal of the non-crosslinked portions of the polymeric coating; and (v) removal of the crosslinked polymeric layer from the immobilized molecule which possesses a complementary structure to exposed residues of such molecule.

This embodiment of the invention is particularly useful for producing polymers having a complementary structure to microbial or other cells. The resultant polymeric compounds can be used as antimicrobial agents, anti-tumor agents, etc.

Still another object of the invention is to provide a method for producing compounds having a complementary structure to a desired compound by the following steps:

(i) selecting and immobilizing a desired molecule to a support;

(ii) contacting the resultant immobilized molecule support with a solution comprising one or more monomers, and optionally further comprising at least one crosslinking agent, and allowing such monomer to associate around exposed residues of the immobilized molecule;

(iii) optionally adding at least one crosslinking agent if not already provided in step (ii) and polymerizing under conditions that result in formation of a molecular coating that possesses a complementary binding structure to the immobilized compound; and (iv) removal of the resultant molecular coating from the support, e.g., by chemical means such as hydrolysis, and cleaving the molecular coating into discrete segments, that possess a complementary binding structure to the immobilized compound.

Another object of the invention is to provide a method for producing a compound, e.g., a polymer or oligomer, having a complementary structure to a desired compound, e.g., a biomolecule, by the following steps:

(i) providing a support onto which has been immobilized a fixed first layer comprising one or more monomers;

(ii) providing on top of said first layer a second layer comprising one or more crosslinkable monomers, wherein such monomers are free to randomly move in the second layer;

(iii) contacting the second layer with a desired molecule, e.g., an enzyme, and allowing for the crosslinkable monomers in the second layer to associate around specific surface residues of such molecule;

(iv) optionally adding a crosslinking agent, to produce a polymeric or oligomeric compound that possesses a complementary structure to exposed residues of such molecule, e.g., residues that constitute the active site of an enzyme; and (v) recovering the resultant compound, e.g., a polymer or oligomer, that possesses a complementary structure to such molecule by dissociation of the layers and removal of the molecule.

In yet another embodiment of the invention, a compound having a complementary structure to a desired molecular entity is produced according to the following steps:

(i) obtaining a desired preformed functionalized polymer, which may be linear or lightly crosslinked; and containing said preformed functional polymer with a desired molecular entity, which may be immobilized or in solution, e.g., a biomolecule such as an enzyme, such that specific functional groups on the polymer interact with the molecular entity;

(ii) allowing for the interactions between the functional groups on the preformed polymer and the biomolecule to equilibrate;

(ii) after equilibration, preserving the resultant complementary structure on the preformed polymer that results after equilibration by one of the following steps:
  (1) altering the functional groups on the preformed polymer that interact least strongly with the molecular entity, e.g., by site-selective chemical modification;
  (2) altering the functional groups on the polymer that interact most strongly with the molecular entity by site-selective chemical modification; or
  (3) crosslinking the polymer; and (iv) thereafter separating the resultant polymer from the molecular entity.

In this embodiment, one or more crosslinkers may be optionally utilized, e.g., irreversible crosslinkers. As noted, the molecular entity that functions as the template may be immobilized to a support or contained in solution.

Another object of the invention is to provide compounds, e.g., polymers or oligomeric compounds, that are complementary in structure to desired molecules or portions thereof, in particular the active site(s). These molecules included in particular biomolecules such as enzymes, receptors, hormones, growth factors, cytokines, antibodies, antigens, lectins, biological cells, cell vesicles, nucleic acid sequences, peptides, glycoproteins, carbohydrates, and fragments thereof.

A more specific object of the invention is to provide compounds, e.g., oligomers or polymers, that are complementary in structure to a desired molecule or portion thereof, e.g., the active site(s) thereof, which may be used, e.g., as agonists and antagonists of enzymes, hormones or receptors; modulators of gene expression, catalysts, therapeutic agents, diagnostic agents, antimicrobial agents, antiviral agents, anti-tumor agents, affinity separation medium, or competitive affinity ligands.

Another specific object of the invention is to use the subject compounds that possess a complementary structure to a desired compound, e.g., a biomolecule or fragment thereof, in any method wherein the use of a compound having a structure complementary to that of another compound or fragment thereof is desirable. These methods will include by way of example diagnostic methods, prophylactic methods, therapeutic methods, and catalyzed syntheses methods.

Still another application is to provide therapeutic, prophylactic or diagnostic compositions which comprise a therapeutically, prophylactically or diagnostically effective amount of a compound according to the invention that possesses a complementary structure to a desired biomolecule or fragment thereof.

BRIEF DESCRIPTION OF THE FIGURES

(FIG. 5E)

FIGS. 6 (1–5) depicts cleavable monomeric crosslinking agents useful in the invention.

In this embodiment, a preformed polymer and a desired molecule are placed in contact, wherein such polymer may be immobilized or in solution. After equilibration, the resultant complementary structure is preserved by chemical means, e.g. by altering specific functional groups or by crosslinking.

In this embodiment, one or more crosslinkers may be optionally utilized, e.g., irreversible crosslinkers.

FIGS. 9 (1–7) depicts the specific monomers and crosslinkers used in Example 2 which demonstrate the use of two-dimensional movement in order to acquire anti-idiotype ligand formation.

FIGS. 10 (1–3) depicts perfluorophenylazide-derivatives (1, 2) and a preassembled scaffold element (3) used in Example 3.

Figure 11:
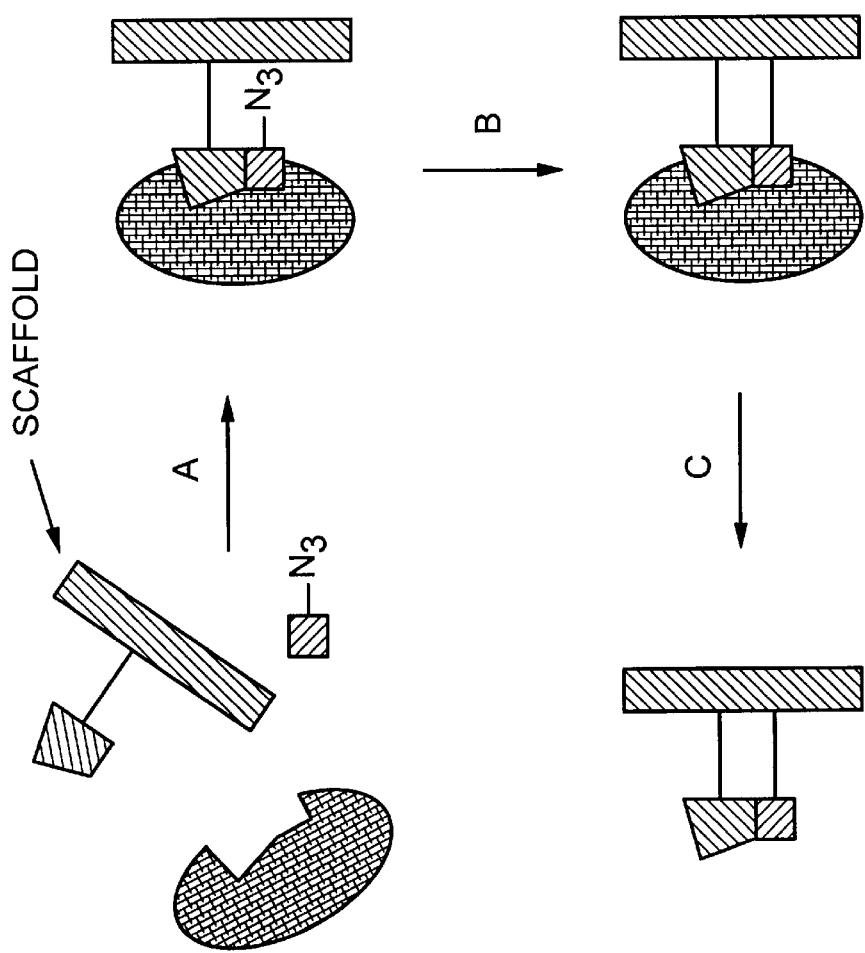

FIGS. 11 (A–C) depict schematically the use of molecular scaffolds to "freeze" a self-assembled complex between ligand providing elements in their interaction with a binding site.

Figure 12:
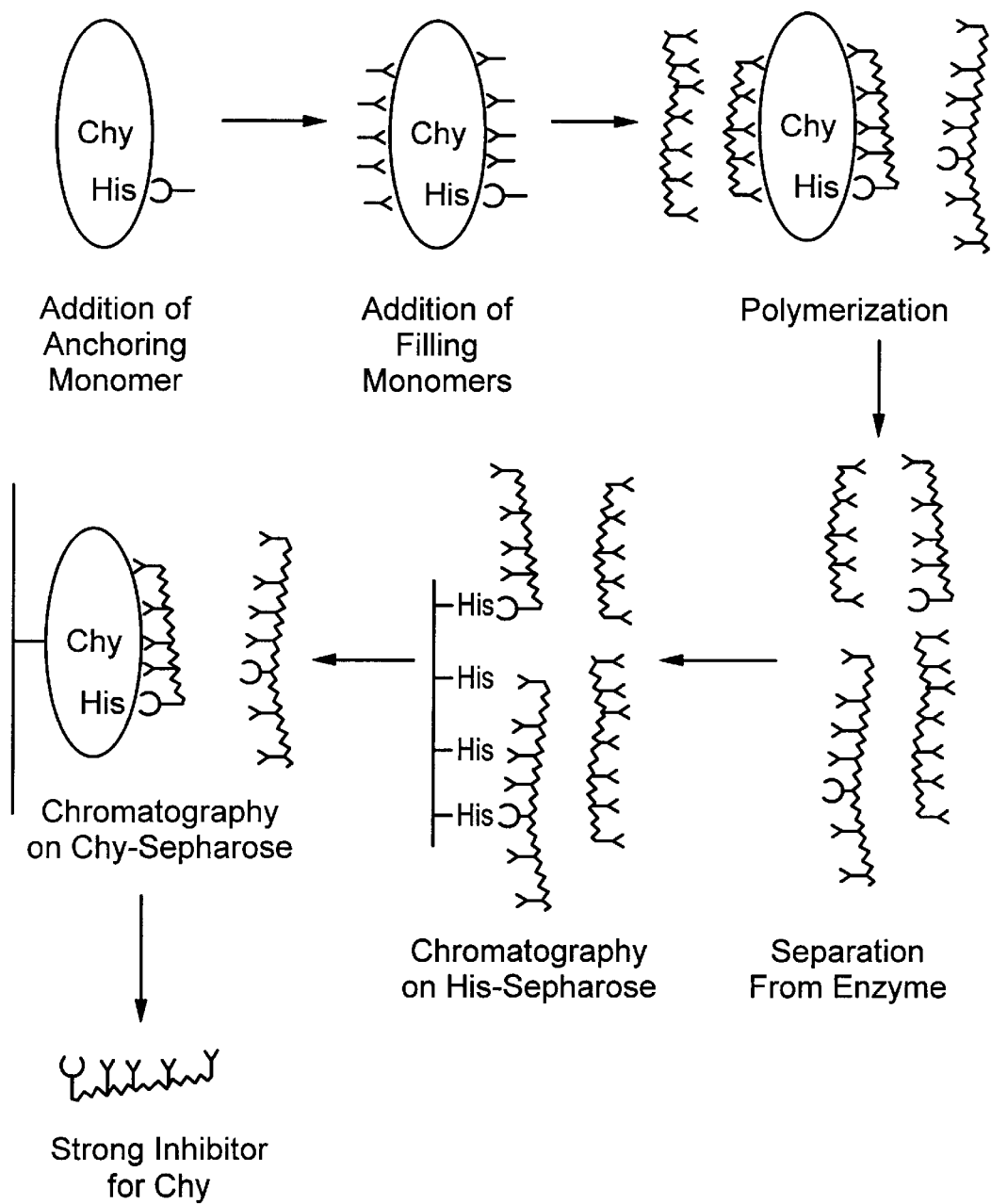

FIG. 12 depicts schematically the synthesis of a polymeric inhibitor of α-chymotrypsin by direct molding of the polymer on the active site of the α-chymotrypsin enzyme.

DETAILED DESCRIPTION OF THE INVENTION

Relationship of Molecular Structure to Function

The present invention is based in part on the fact that the activity of molecules, and in particular biomolecules, is correlated to their structure, which affects their ability to specifically interact with other molecules, e.g., receptors, hormones, enzymes, nucleic acid sequences, and microorganisms.

When the binding partner of a compound such as a protein is known, it is relatively simple to study the interaction of the compound and its binding partner, and how such binding interaction affects biological activity. Moreover, one can screen compounds for their ability to competitively inhibit the formation of compound-binding partner complex or to dissociate such complex. Compounds which inhibit complex formation and stability of such complexes are likely to affect the biological activity of the particular compound, if they can be effectively delivered to the target site of compound-ligand interaction.

Generally, it is only specific residues of the compound which interact with other moieties, e.g., other biomolecules. These residues are generally on the surface of the particular compound, e.g., an enzyme, biological cell, receptor, etc.

Moreover, these residues in turn generally interact with specific residues which are likewise exposed on the surface of a binding partner, e.g., another biomolecule. In the case of proteins, these residues typically only comprise relatively small surface portions of the molecule.

These residue binding interactions which affect biological activity and may result in a reaction proceeding and the formation of a covalent bond are the consequence of the aggregate effects of various non-covalent interactions, including the formation of salt bridges, hydrogen bonds, van der Waals forces and other electrostatic interactions. Also, hydrophobic interactions are important in stabilizing the conformation of biomolecules such as proteins, and thus indirectly affect ligand binding, although hydrophobic residues are usually buried and are not part of the binding site.

Thus, if it were possible to directly produce a compound comprising specific residues that specifically interact with such surface residues of a desired compound, e.g., a biomolecule, such compounds would be highly useful since they will likely affect the biological activity of the desired compound. Moreover, direct production would be further advantageous in that it would eliminate, or at least substantially reduce the need for highly complex and often fruitless drug screening methods. Moreover, such direct production would potentially give rise to compounds having enhanced properties in relation to compounds produced by conventional methods, e.g., enhanced solubility, stability, activity, affinity and/or avidity relative to ligands isolated from conventional sources.

Molecular Imprinting Technology

The present invention is based in part on the inventors' previous extensive research and knowledge in the area of molecular imprinting. This technique is reviewed in *Biotechnology*, Vol. 14, pp. 163–170 (February 1996), from which much of this discussion is based.

Figure 1:
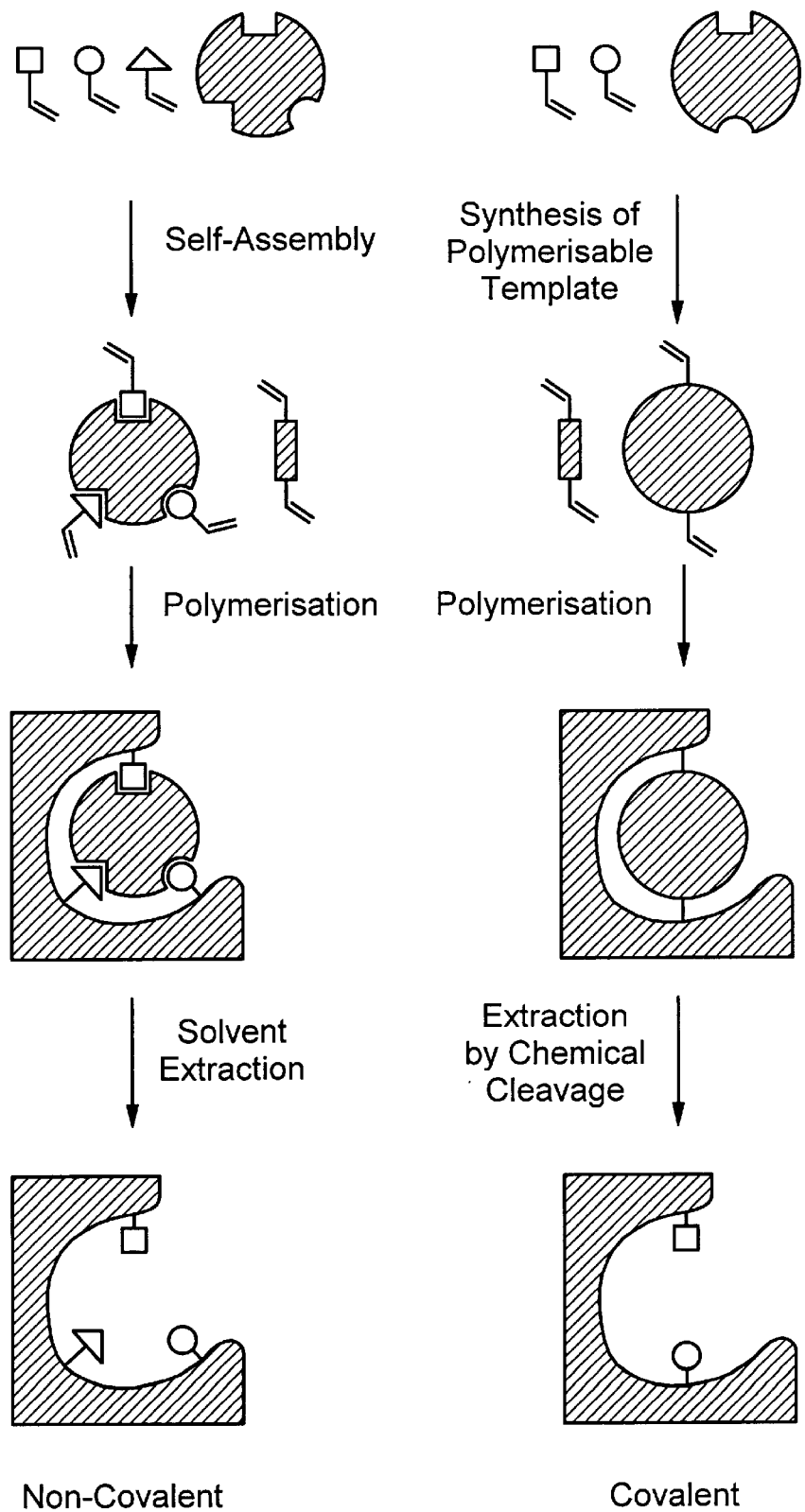
FIG. 1 schematically represents imprint formation by non-covalent and covalent approaches.

The concept of molecular imprinting is depicted in FIG. 1. The molecule to be imprinted is first allowed to form bonds with polymerizable entities, which are subsequently crosslinked. Following extraction of the print molecule, specific recognition sites are left in the polymer where the spatial arrangement of the polymer network corresponds to the imprinted molecule. These procedures make use of a high percentage of crosslinker resulting in the formation of rigid and insoluble macroporous polymers. This template-assisted assembly, leading to an artificial recognition matrix, is thus performed in a very direct way.

The covalent approach requires a polymerizable derivative of the imprint species that is subsequently incorporated into the polymeric matrix during polymerization. These covalent bonds must be cleavable. The most common types of linkages are either esters of carboxylic/boronic acids, ketals or imines (Schiff bases). The necessary synthetic routes to accomplish such derivatives constrain the versatility of the approach and reduces the number of species that can be imprinted. After the polymer is formed, the imprint species is extracted by cleavage of these covalent bonds, usually by acid hydrolysis. Rebinding of the imprint species to the matrix is then achieved by re-establishing the covalent bonds between the print molecule and the matrix.

The other, non-covalent approach exclusively uses non-covalent interactions in the recognition of the imprint species. The greater the variety of interactions that are available between the imprint species and the functional monomers, the better the artificial binding site becomes. Typical interaction types that have been exploited are ionic interactions, hydrogen bonds, π-π-interactions, and hydrophobic interactions. Since they are strongly dependent on the polarity of the solvent, the best imprints are made in organic solvents such as chloroform or toluene. When these normally weak interactions have been established in solution, polymerization is initiated and a porous polymeric matrix is formed around the imprint species. The formed macromolecular architecture is thus complementary to the shape and function of the imprint species. After polymer formation the imprint molecule can be almost quantitatively recovered by mild extraction from the matrix. Association and dissociation of the original print molecule to the artificial binder takes place without requiring any covalent bond formation or cleavage. The target molecule simply diffuses in and out of the complementary sites.

Because the limited number of synthetic alternatives for reversible covalent interactions reduces the flexibility of this technique, the non-covalent protocol may be more versatile. The use of non-covalent interactions allows for the selection of several different monomers for simultaneous interaction with the imprint molecule. This in turn leads to a higher degree of selectivity of the imprinting site. A judiciously chosen "cocktail" of monomers may be the best way of making tailor-made artificial binding sites.

Imprint molecules carrying groups that can bind to metals, e.g., the imidazole groups of histidine, can be used to coordinate polymerizable metal chelators. This metal coordination approach has been recently evaluated. A combination of covalent and non-covalent approaches may be advantageous for molecules that seem difficult to imprint. In the case of the steroid cholesterol the single hydroxyl group was modified to a carbonic ester, allowing its incorporation into the polymer using the covalent imprinting approach. Subsequent rebinding of cholesterol was performed using only non-covalent forces, after cleavage of the template. A potential problem with this attractive protocol is that the binding site is changed by the chemical modification of the site after hydrolysis. Thus, there is the risk of reducing the site selectivity.

A large number of substances have been imprinted for various practical applications. Four main applications include the use of molecularly imprinted polymers: (i) as tailor-made separation materials, (ii) as antibody and receptor binding site mimics in recognition and assay systems, (iii) for catalytic applications as enzyme mimics, and (iv) as recognition elements in biosensors.

However, the use of such techniques for direct synthesis of drugs and in vivo prophylactic or diagnostic agents has not previously been suggested. Based on their extensive knowledge and expertise in molecular imprinting, the present inventors conceived the idea that it should be possible to directly synthesize a compound, e.g., a polymer or oligomer, that possesses a complementary structure to a desired compound, e.g., biomolecule, or portion thereof, and use the resultant compound in applications wherein a compound having a complementary structure to a biomolecule would be desirable, e.g. therapeutic applications. As discussed, the ability of most biomolecules to function as therapeutic or diagnostic agents hinges upon its structure, and the interaction of such structure with other molecules. Therefore, the present invention provides compounds, e.g., polymers or oligomers, useful as drugs, both prophylactic and therapeutic agents and in vivo diagnostic agents. The compounds produced according to the invention are useful as therapeutic or diagnostic agents based on their ability to specifically interact with and affect the biological activity of a particular biomolecule that possesses a complementary structure to such compound.

In general, the synthesis of a compound that affects the activity of a particular compound will be effected by a method comprising:

(i) selecting a molecule, preferably a biomolecule such as an enzyme, the activity of which is desirably to be affected (inhibited or enhanced);

(ii) contacting such molecule, which may or may not be immobilized, with one or more monomers that associate with specific residues of such molecule via covalent or non-covalent interactions;

(iii) polymerizing the monomers which are associated around such compound optionally in the presence of a crosslinking agent, which may be cleavable, under conditions that result in a molecular network ("coating") that is comprised on the surface of such compound, wherein such molecular network possesses a complementary structure to the selected compound or specific portion(s) thereof; and (iv) removing the molecular network (coating) from the selected molecule, and cleaving the molecular coating into smaller moieties, as required, to produce a compound that possesses a complementary structure to or a portion(s) thereof and which compound is suitable for affecting the activity of such compound, e.g., when used as a therapeutic or in vivo diagnostic.

Thus, in the present invention, similar to molecular imprinting, polymerizable molecules are permitted to associate by complementary binding (non-covalent or covalent) to specific groups of a biological compound followed by polymerization. However, an important difference of the present invention is that the resultant polymers or oligomers form a coating or image around the biomolecule, which coating or image is removed therefrom, and discrete entities are derived therefrom, which may be used, e.g., as therapeutic or prophylactic agents, i.e., drugs.

Also, another important difference between the polymers or oligomers that result from the subject invention in relation to the products that result from traditional molecular imprinting methods is their size. In general, the polymeric or oligomeric compounds that result from the methods of the present invention will possess a molecular weight that ranges from about 1000 to 200,000, more preferably from about 5,000 to 50,000, and most preferably about 20,000 to 30,000. However, these ranges may dependent upon factors such as the particular method utilized to produce such compounds, the particular template molecule, and the intended application therefor. Generally, if the polymer or oligomer is to be utilized as an in vivo therapeutic or diagnostic, it will possess a molecular weight on the lower end of the above ranges. In general, polymers according to the invention will comprise over 100 repeat units and oligomers will comprise less than about 100 repeat units. This controls the molecular weight. As noted above, lower molecular weights are preferably particularly for therapeutic purposes wherein solubility and viscosity are a significant concern. The upper limit of the preferred molecular weight range will correspond to polymers having about 200–300 repeat units. However, this may vary dependent upon the particular monomers and the intended application thereof.

Another difference between the polymers or oligomers that result from the subject invention in relation to conventional molecular imprinting methods is their size. In general, the subject polymers or oligomers will be smaller. The specific size will vary dependent upon the particular method utilized. Preferably, the polymeric or oligomeric compounds will possess an average chain length ranging from 25 angstroms to 5000 angstroms, more preferably from about 250 to 2500 angstroms, and most preferably about 500 to 1500. This will vary depending upon the intended application. If the polymeric or oligomeric compounds are to be used therapeutically they will typically be of smaller size, e.g., from about 500 to 1000 angstroms, or smaller. Alternatively, the subject compounds can be used in vitro, e.g., as affinity separation media or competitive affinity ligands.

As discussed above, the present invention contemplates different methods for producing the subject polymeric or oligomeric compounds that possess a complementary structure to a desired molecular entity, e.g., a biomolecule. Some of these methods are depicted schematically in FIGS. 2, 3, 5, 7, 8, 11 and 12.

Figure 2:
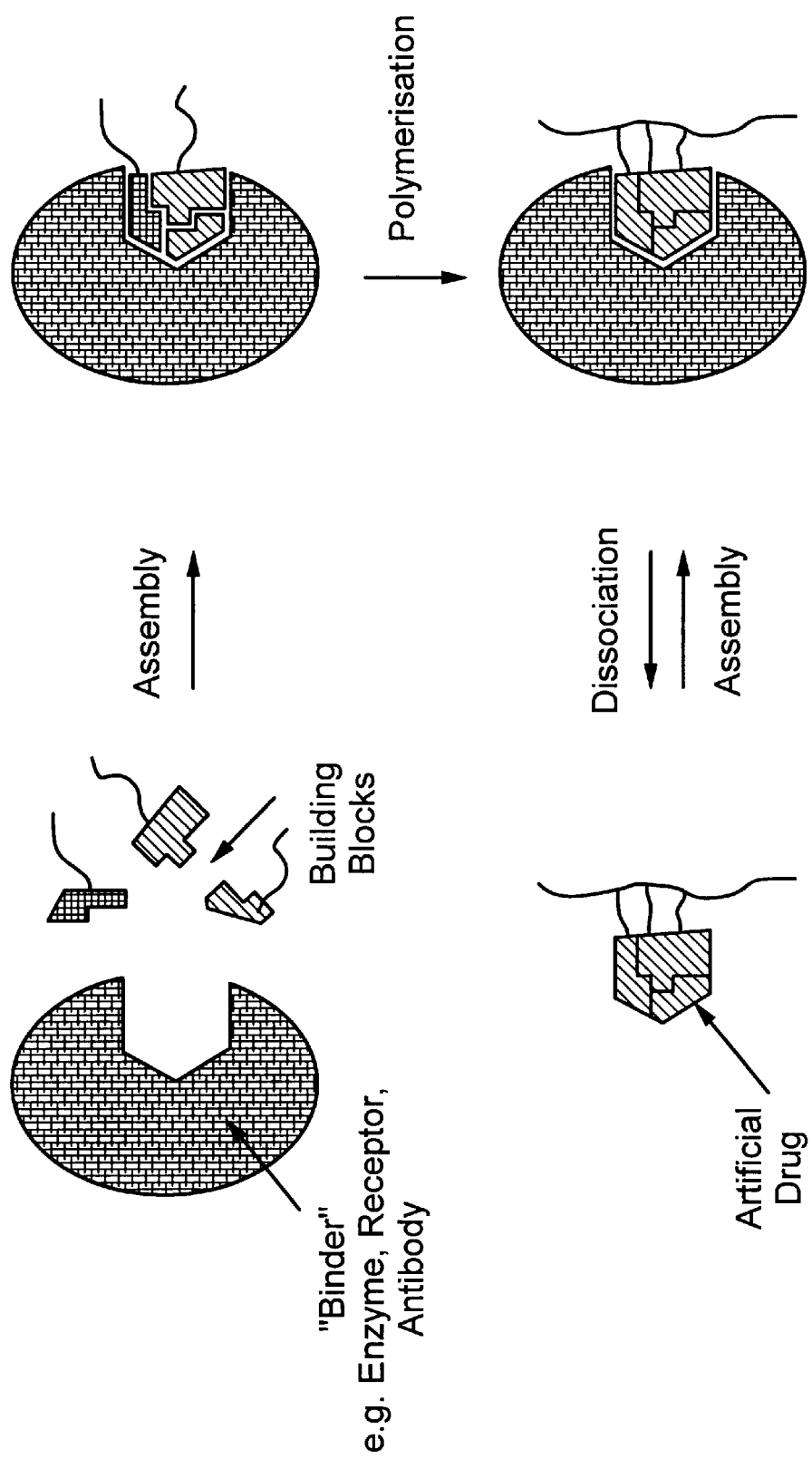
FIG. 2 depicts schematically the production of a polymeric or oligomeric compound having a complementary structure to a biomolecule, e.g., an enzyme, receptor or antibody. In this schematic, monomers or other molecules are allowed to align along the surface or active site of a biomolecule, based on their complementary structure to residues on the biomolecule. These residues may comprise endogenous functional groups which alternatively may be derivatized. After alignment, these monomers are polymerized, optionally in the presence of a crosslinking agent. The biomolecule is removed to produce a thin-layer polymeric or oligomeric compound that exhibits a complementary structure to the active site of the biomolecule.

For example, FIG. 2 depicts schematically an embodiment wherein an oligomer or polymer having a complementary structure to the active site of a molecule, e.g., a biomolecule such as an enzyme, is produced. In this method, monomers or other molecules are permitted to align along the surface or active site of a biomolecule, based on their complementary structure, to residues on the molecule, e.g., those in the active site of a biomolecule. These residues may comprise functional groups, which alternatively may be derivatized. After alignment, the monomers are polymerized, optionally in the presence of a crosslinking agent. The biomolecule is then removed to produce a thin-layer polymeric or oligomeric compound that possesses a complementary structure to a portion of the selected molecule, e.g., active site of a biomolecule.

Figure 3:
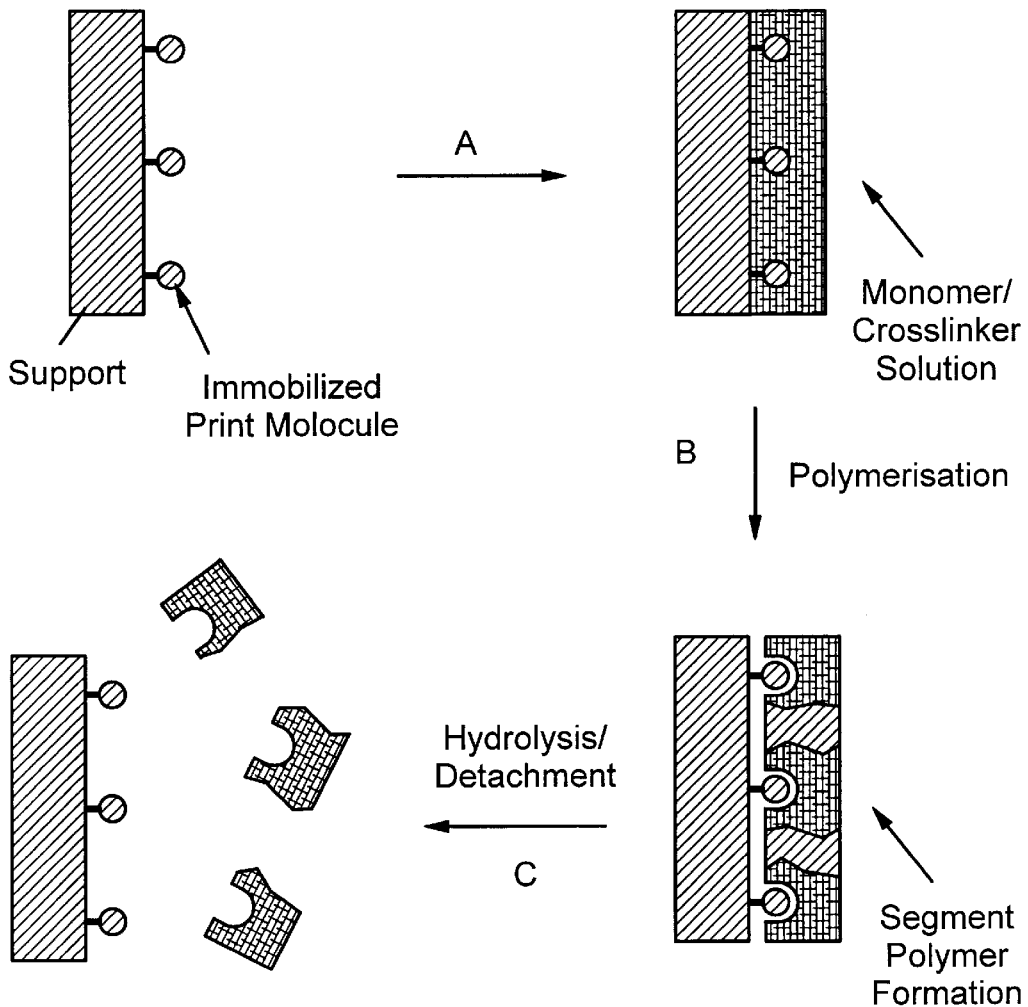
FIGS. 3(A–C) schematically represents another means for producing polymeric compounds that are complementary in structure to desired molecular entities. In this method, desired molecules are immobilized to a support, contacted with complementary monomer(s) and crosslinker(s), and polymerization effected, to produce a "segment polymer," which segments are subsequently removed from the support, e.g., by hydrolysis or cleavage.
Figure 4:
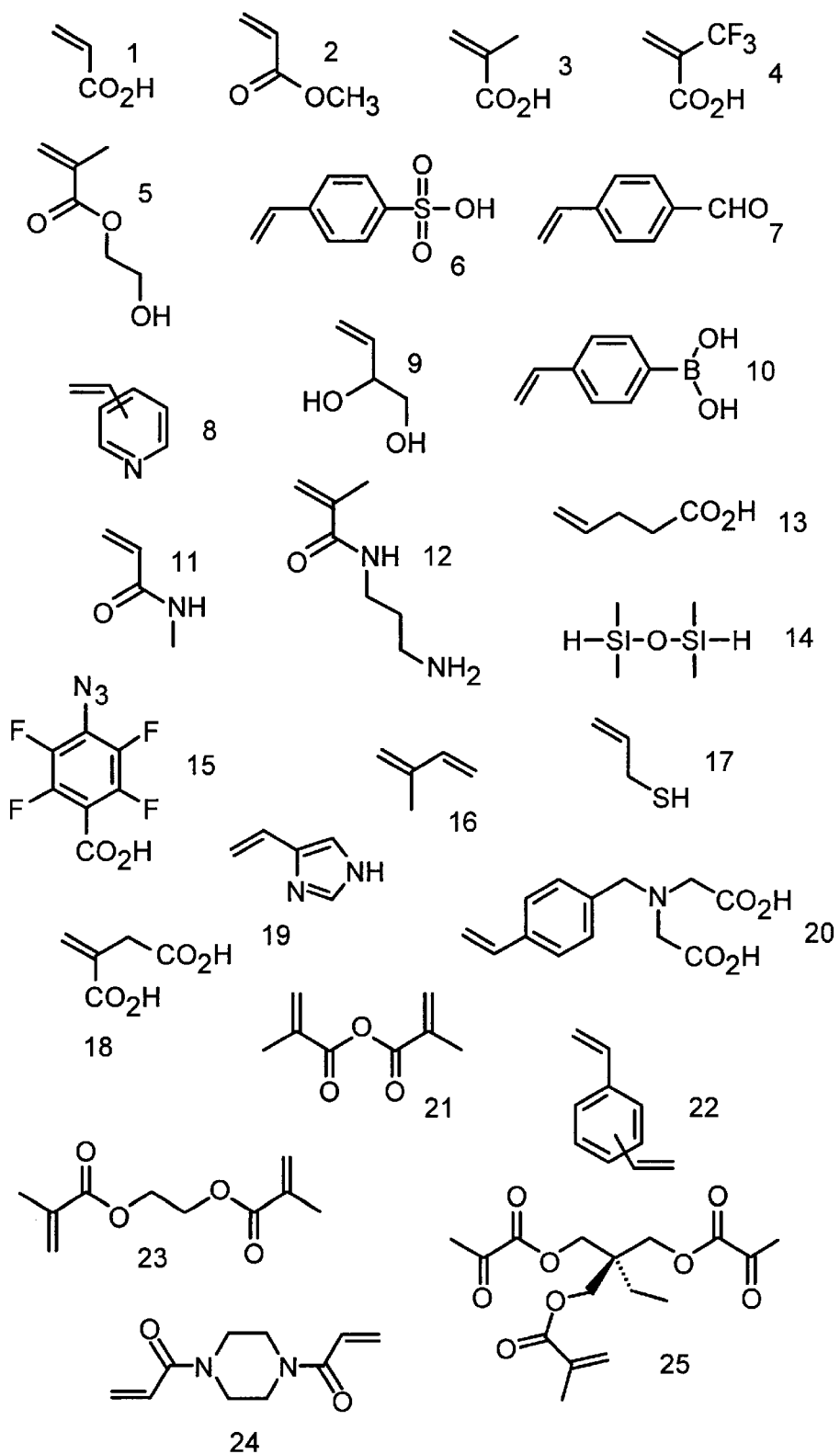
FIGS. 4 (1–25) shows examples of crosslinkable and non-crosslinkable monomers which are useful in the present invention.

FIG. 3 depicts another preferred means of practicing the invention. In this method, a desired moiety ("print molecule") is immobilized to a support, e.g., a polyacrylamide gel or other support material. (Other support materials include by way of example silica, polysaccharides, organic polymers, metals, alloys and glass, et seq.). This molecule may be immobilized to the support by covalent or non-covalent means. After immobilization the support comprising an immobilized print molecule, e.g., an enzyme, receptor, nucleic acid sequence, or other biomolecule is contacted with a solution containing one or more monomers. The monomers are preferably selected such that they are functionally complementary to functional groups comprised on the immobilized print molecule. For example, if the print molecule contains positively charged moieties, then negatively selected monomers are preferably selected. Typically, the monomer containing solution will comprise crosslinkers.

These monomers are permitted to move and become associated around the immobilized print molecule. Thereafter, polymerization is allowed to proceed. Crosslinking agent is preferably added during polymerization if not already present in the monomer solution. The polymerization is conducted under conditions that provide for the associated monomer to maintain a complementary structure to the immobilized print molecule, e.g., an enzyme.

Polymerization will result in the formation of "segment" polymers as shown in FIG. 3B. After polymerization, the resultant oligomeric or polymeric segments are released from the solid support, e.g., by hydrolysis. It is important that the polymer be cleaved into smaller molecules, e.g., oligomers, which are suitable, e.g., as therapeutic agents. This may be accomplished by the use of cleavable crosslinkers. Suitable examples thereof include, but are not limited to, cleavable crosslinkers such as analogs of bis-acrylamide, such as bis-acrylcystamine, N,N-diallyltartardiamide, N,N-(1,2-dihydroxyethylene)bisacrylamide, or N,N'-bis-(acryloyl)cystamine, N1-(E)-1-(4-vinylphenyl) methylidene)-4-vinyl aniline, allyl disulfide, bis(2-(methacrylgyl, oxyethyl))disulfide.

Figure 5:
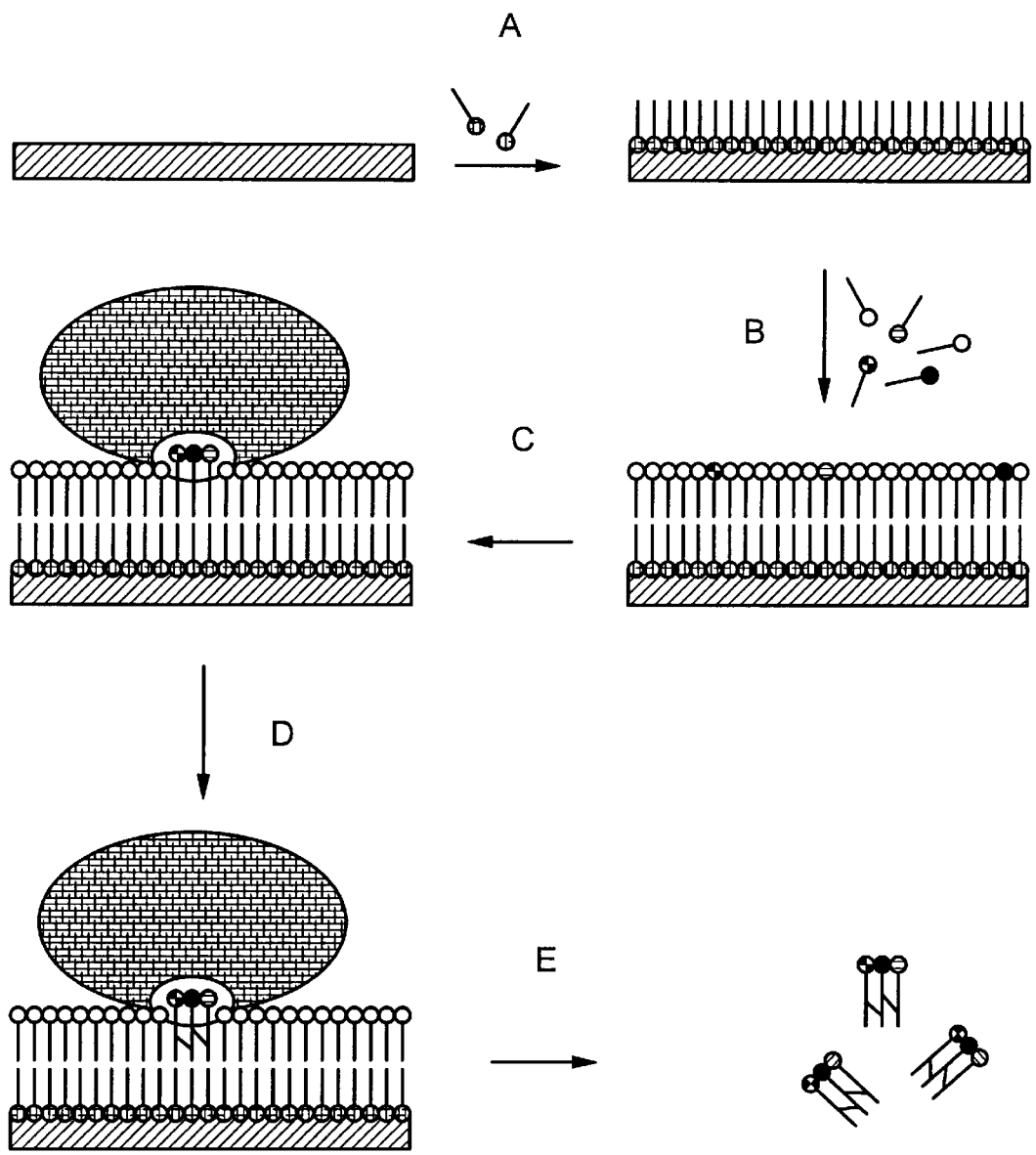
FIGS. 5(A–E) depicts schematically the production of a compound having a complementary structure to the binding site of a molecule, e.g., a biomolecule sequence or enzyme. In this method (see 5C), monomers in the uppermost layer orient themselves in a complementary manner around specific exposed residues of the biomolecule, and these monomers are "frozen" in this complementary arrangement by crosslinking, and the biomolecule removed to produce a plurality of oligomeric or polymeric compounds that possess a complementary structure to a portion (e.g., active site) of the selected molecular entity, such as an enzyme (see 5D). After breakage ofd the layers, and removal of the enzyme, structures remain that are complimentary to the active site.

Yet another means of practicing the invention is depicted in FIG. 5. This embodiment is particularly suitable for producing polymeric or oligomeric compounds that selectively interact with the active site of a biomolecule.

In this embodiment of the invention, a fixed polymeric monolayer constituted of particular monomers is produced. For example, this fixed monolayer may consist of long-chain alkyl thiols as shown in FIG. 9,1. Onto this fixed polymeric monolayer, a second layer is made which will be constituted of desired monomers, and crosslinkable monomers. For example, this second layer may comprise long-chain alcohols having the structure shown in FIG. 9,2 and the crosslinkable, functional alkenyl-structures shown in FIGS. 9,3–6. Unlike the first layer, the molecules are freely able to move within the second layer in a random manner.

A desired biomolecule, e.g., an enzyme, is placed on top of the second layer. This results in a directed arrangement of the functionalized crosslinkable monomers around specific surface residues of the biomolecule, e.g., the active site of an enzyme or other protein. For example, the active site of an enzyme such as acetylcholine may be placed in contact with the second layer resulting in the complexation of the functional alkenes with specific residues on the enzyme. Thereafter, polymerization is allowed to proceed by the addition of a crosslinking agent, such as tetramethyldisiloxane. This results in the formation of a crosslinked polymer that is complementary in structure to the active site of the biomolecule, e.g., an enzyme such as acetylcholine esterase.

Thereafter, the two layers on the support are cleaved, and the biomolecule, e.g., an enzyme is removed resulting in the formation of a polymeric or oligomeric compound that is complementary in structure to the active site of the biomolecule, e.g., acetylcholine esterase.

Figure 7:
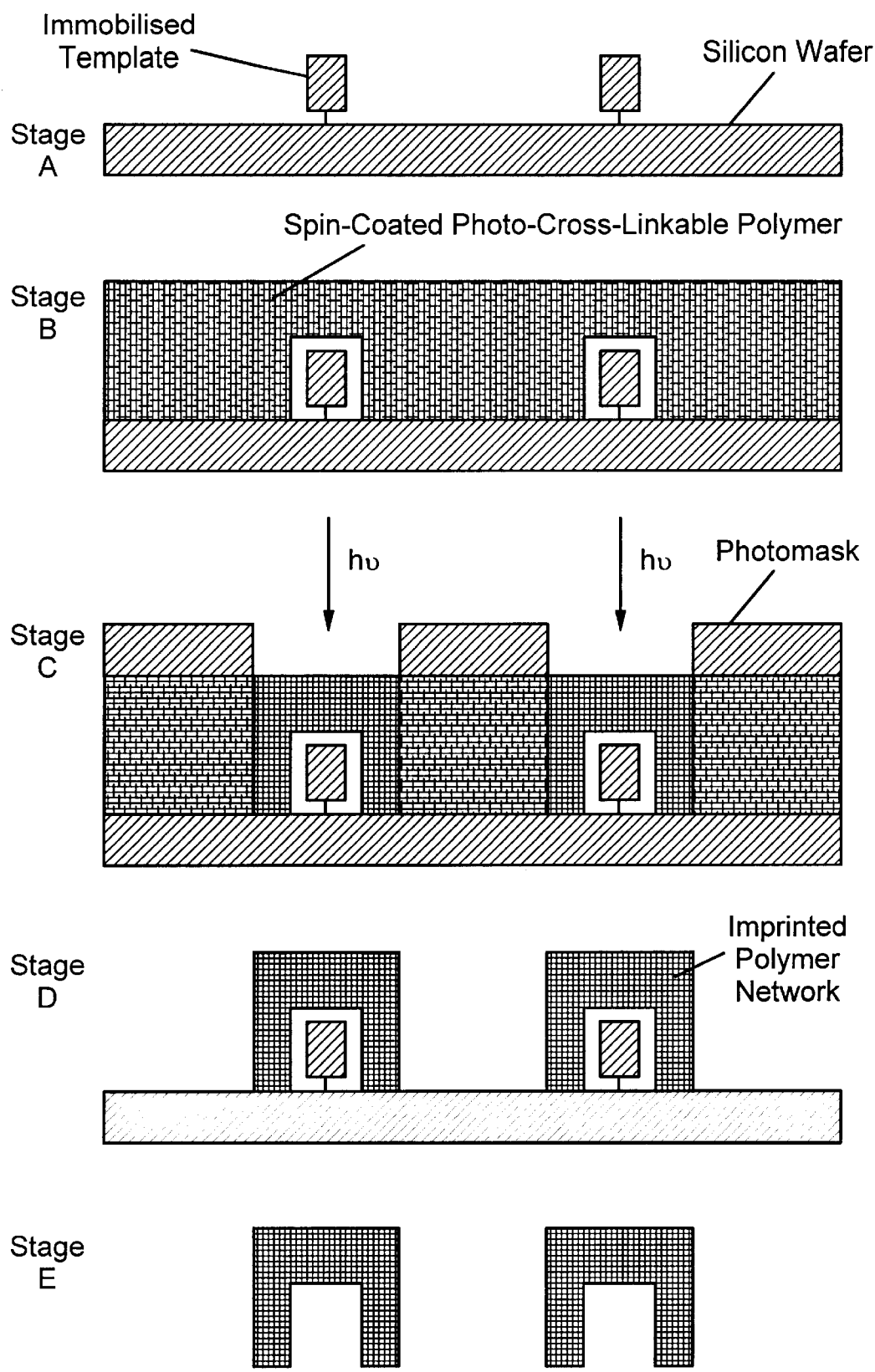
FIGS. 7 (A–E) schematically represents a means for producing polymer coatings that are complementary in structure to large biological moieties, e.g., cells. In this method, selective crosslinking of specific areas that surround immobilized biomolecules is effected by the use of irradiation and a photomask.

In another preferred embodiment depicted schematically in FIG. 7, a desired molecule, e.g., a microbial or mammalian cell is immobilized to a support, e.g., a thin layer support such as a silicon wafer. After immobilization, the support, including the immobilized biological molecule, is then coated with a desired polymer. This may be accomplished by known methods.

In this embodiment, a polymer is selected which is crosslinkable under conditions that enable selected areas of the polymer coating to be crosslinked. For example, this may be effected by the use of photocrosslinkable polymers.

In particular, the regions of the polymer coating which surround the immobilized compound are selectively crosslinked. This may be effected by the use of a photomask to protect specific areas not in direct contact with the immobilized molecule, e.g., a bacterial or mammalian cell, and the use of irradiation to initiate crosslinking of the non-protected areas surrounding the molecule, e.g., a particular cell. This results in an imprinted polymer network which surrounds (coats) the immobilized biological moiety. This imprinted polymer coating is then removed from the solid support. This polymeric coating will possess a complementary structure to exposed residues of the immobilized moiety, e.g., a cell. This polymeric material therefore may be used to affect the activity of the immobilized moiety, e.g., a microbial or mammalian cells. For example, it should be useful as an antimicrobial agent, which should inhibit such cells from infecting susceptible cells. Also, it should be useful as a cell separation agent.

This polymeric material also may be attached to other materials, e.g., therapeutic and/or diagnostic agents in order to target such materials to desired cells, e.g., mammalian tumor cells or the site of infection.

This embodiment of the invention, because it requires the crosslinking of specific areas, e.g., by the use of a photomask, is not practical for small molecules, such as active sites. Rather, it is best suited for larger biological moieties such as microbial and mammalian cells as well as biological surfaces, e.g., tissues.

Figure 8:
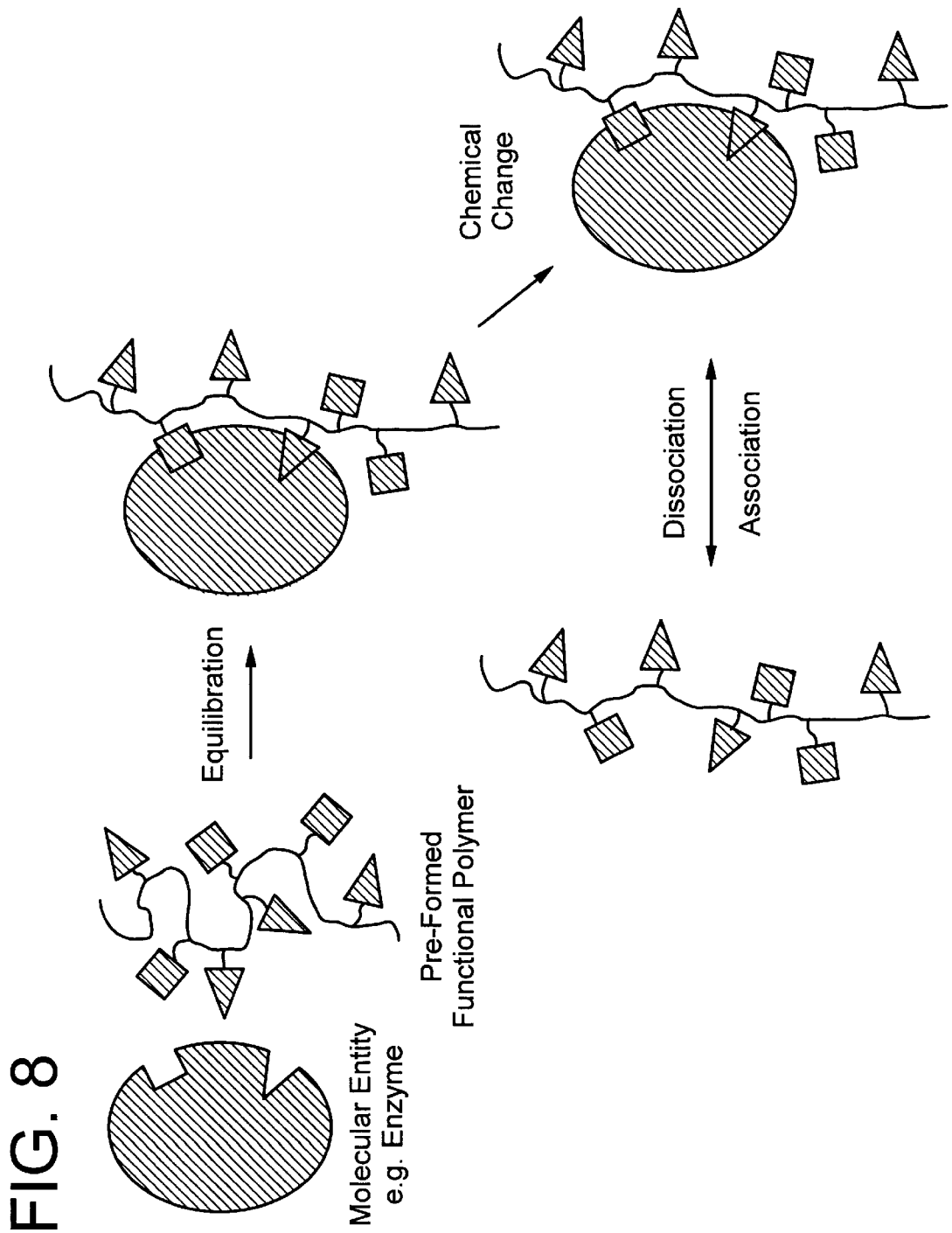
FIG. 8 schematically depicts another embodiment of the invention.

In yet another embodiment of the invention depicted schematically in FIG. 8, a molecular entity is allowed to interact with a preformed functional polymer which can either be linear or lightly crosslinked. The pre-formed functional polymer can interact with the molecular entity via covalent and/or non-covalent bonds (FIG. 8). After equilibrium, either (a) those functional groups on the polymer which interact least strongly with the molecular entity are chemically altered by, for example, site-selective chemical modification, or (b) those functional groups on the polymer which interact most strongly with the molecular entity are chemically altered by, for example, site-selective chemical modification, or (c) crosslinking of the polymer can be preformed. Thereafter the polymer is separated from the molecular entity which acted as a molecular template and purified via an appropriate procedure. In this embodiment the molecular entity used as a template may exist freely in solution or alternatively be immobilized onto a suitable support and, optionally, one or more crosslinkers may be used, one or more of which may be reversible crosslinkers.

In still another embodiment of the invention, depicted schematically in FIG. 11, a complementary structure to a desired molecule, e.g., an enzyme, is produced using molecular scaffolds that function to "freeze" a self-assembled complex between ligand building elements in their interaction with a portion of a template molecule, e.g., active (binding) site of an enzyme. In this embodiment, a desired molecule, e.g., an enzyme such as crosslinked trypsin, is mixed together with derivatized ligand building elements, e.g., the perfluorophenylazide-derivatives shown in FIG. 10, which are judiciously selected such that they fit within the active site of such molecule.

Thereafter, these ligand elements including the scaffold-bearing element, are induced to specifically (rather than randomly) interact with the molecule by effecting such interaction in a suitable solvent system. For example, in order to reduce non-specific hydrophobic interactions, the process can be effected in a polar solvent such as acetonitrile. After these specific interactions have occurred, the self-assembled complex between the ligand building elements and the active site is "frozen," e.g., by exposure to UV radiation which result in the azido-functionalities becoming inserted into the amino-functionalities of the scaffold. (See 11C). Thereafter, the resultant active site-binding conditions are separated from the random binding adducts, e.g., by affinity chromatography.

In still another embodiment of the invention, depicted schematically in FIG. 12, the invention provides for the direct synthesis of a compound complementary to the active site of a compound, e.g., an enzyme, by directly molding a polymer onto the active site of said enzyme. In this embodiment, an anchoring monomer is allowed to interact with the molecule, e.g., an enzyme such as α-chymotrypsin, as well as a filling monomer (that fills active site thereof) such as methacrylamide or methacrylic acid. Polymerization is then initiated, e.g., by UV irradiation. The resultant polymeric or oligomeric compounds that surround the compound are then separated from the compound, e.g., an enzyme, by hydrolysis. Thereafter, the desired polymeric or oligomeric compounds are isolated, e.g., by affinity chromatography. For example, affinity chromatography can be effected using a support that specifically interacts with the anchoring monomer, e.g., a His sepharose support. The non-bound portion is discarded, and a second affinity chromatography can be effected using an affinity support containing the template molecule, e.g., α-antitrypsin. The resultant polymeric or oligomeric compounds are then eluted from the support and tested for activity, e.g., inhibiting activity against α-chymotrypsin using a standard activity assay using BTEE.

As discussed, the subject invention provides compounds, i.e., polymers or oligomers, that exhibit a complementary structure to desired molecules, e.g., biomolecules, or portions thereof, e.g., the active site. These compounds are useful as in vivo or in vitro therapeutic or diagnostic agents based on their ability to affect the activity of a particular biomolecule, e.g., a protein, DNA, virus, receptor, hormone, enzyme glycoprotein, microbial cell, mammalian cell, etc. Also, these compounds may be used as competitive affinity ligand inhibitors, competitors, agonists, catalysts, or antagonists. These uses are meant to be exemplary and not exhaustive of the applications of the compounds which result from the present invention. Essentially, the subject compounds can be used for any purpose wherein a compound having a complementary structure to another compound is useful.

I. Selection or Functional Monomers for Production of Subject Oligomeric or Polymeric Compounds The polymerization reaction mixture for the preparation of the subject complementary compounds usually consists of a desired molecule, e.g., a biomolecule, polymerizable functional monomers, an effective amount of one or more crosslinking agents which enable formation of a sufficiently rigid polymeric or oligomeric structure, inert solvent, and a free radical or other polymerization initiator if necessary to initiate polymerization. Mixtures of monomers and crosslinking agents can be used in the polymerization method.

Two approaches to the production of a molecular imprint polymer have been developed, and either can be used in the methods disclosed herein. In the first method, a biomolecule is covalently bound to a polymerizable monomer, and after polymerization, the covalent bond is cleaved to release the biomolecule from the polymeric coating. Using this method, a selected biomolecule is attached to a polymerizable moiety using any appropriate method. The polymerizable biomolecule should contain a linkage that can be broken to release the biomolecule after the polymeric compound is formed, without adversely affecting the complementary structure thereof. The resultant polymer compound shall be cleavable into discrete entities suitable for in vivo use.

In the second method, polymerizable monomers arrange themselves about a biomolecule based on non-covalent interactions (such as ionic, hydrophobic, steric, electrostatic, and hydrogen bonding interactions), and after polymerization, the non-covalently bound biomolecule is simply leached out.

Any suitable combination of functional monomers, crosslinkers and initiators that provide an accurate imprint of the biomolecule on polymerization (a polymer compound confirming a complementary structure) is suitable for use in the present invention.

In general, the imprinted compound should exhibit as closely as possible the reverse topology of the biomolecule. For example, if the biomolecule has an anionic group at a specific location that is important to the desired biological activity of the mimic, the imprinted polymeric compound should have a cationic group at that location. If the biomolecule has a cationic group at a specific location that is important to the desired biological activity of the biomolecule, the polymeric compound imprint should have a anionic group at that location.

Preferred classes of monomers and specific monomers include, but are not limited to, the following classes and derivatives thereof: acrylic acid and derivatives (e.g., 2-bromoacrylic acid, acryloyl chloride, N-acryloyl tyrosine, N-acryoyl pyrrolidinone), acrylates (e.g., alkyl acrylates, allyl acrylates, hydroxypropyl acrylate), methacrylic acid and derivatives (e.g., itaconic acid, 2-(trifluoromethyl) propenoic acid), methacrylates (e.g., methyl methacrylate, hydroxyethyl methacrylate, 3-sulfopropyl methacrylate sodium salt), styrenes (e.g., (2, 3 and 4)-aminostyrene, styrene-4-sulfonic acid, 3-nitrostyrene), vinyls (e.g., vinyl chloroformate, 4-vinylbenzoic acid, 4-vinylbenzaldehyde, vinyl imidazole, 4-vinylphenol, 4-vinylamine, acrolein), vinylpyridines (e.g., (2, 3, and 4)-vinylpyridine, 3-butene 1,2-diol), boronic acids (e.g., 4-vinylboronic acid), sulfonic acids (e.g., 4-vinylsulfonic acid), metal chelators (e.g., styrene iminodiacetic acid), acrylamides and derivatives (e.g., N-methyl acrylamide), methacrylamides and derivatives (e.g., N,N-dimethyl acrylamide, N-(3-aminoprpoyl) methacrylamide), alkenes (e.g., 4-pentenoic acid, 3-chloro-1-phenyl-1-propene) (meth)acrylic acid anhydride and derivatives (e.g., methacrylic anhydride), silicon-containing monomers (e.g., (3-methacryloxypropyl)trimethoxy silane, tetramethyldisiloxane), polyenes (e.g., isoprene, 3-hydroxy-3,7,11-trimethyl-1,6,10-dodecatriene), azides (e.g., 4-azido-2,3,5,6-tetrafluorobenzoic acid), thiols (e.g., allyl mercaptan). Acrylate terminated or otherwise unsaturated urethanes, carbonates and epoxies can also be used in this present invention, as can silicon-based monomers.

If utilized, the crosslinking agent or agents will preferably be one or several polymeric or oligomeric compound, or a compound that provides for cleavage under specific conditions.

Crosslinking agents that lend rigidity to the subject polymeric compounds are known to those skilled in the art, and include, but are not limited to, di-, tri-, tetra- and penta-functional acrylates, methacrylates, acrylamides, vinyls, allyls, and styrenes. Examples of reversible, cleavable crosslinkers which are useful in this invention include, but are not limited by, N,N'-bis-(acryloyl)cystamine, N,N-diallyltartardiamide, N,N-(1,2-dihydroxyethylene) bisacrylamide, N1-((E)-1-(4-vinylphenyl)methylidene)-4-vinylanilene, allyl disulfide, and bis(2-methacryloyloxyethyl))disulfide.

Any ratio of simple monomers to crosslinking monomers can be used that provides a polymeric structure of appropriate integrity, e.g., that can be used in vivo. Those skilled in the art can select suitable ratios of monomers to provide the desired structural integrity.

In the case of polymeric or oligomeric compounds that are to be utilized in vivo as therapeutics or diagnostics, it is important to select monomers that are non-toxic and which exhibit suitable in vivo stability and solubility. Preferred examples include, but are not limited to, acrylamides and acrylates. Alternatively, the polymer may be treated post-polymerization to enhance solubility, e.g., by reaction with suitable organic molecules.

Different polymerization methods may be used including free radical, cationic, and anionic polymerization. Polymerization conditions should be selected that do not adversely affect the active conformation of the compound for which a complementary polymeric compound is to be produced.

Preferred monomers useful in the invention are reversibly crosslinking monomer containing Schiff s base linkages. These compounds are depicted below:

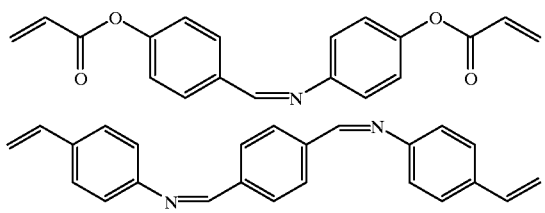

Crosslinkers Containing Schiff's Base-linkages

Another possibility is the use of disulfide containing analogs of bis-acrylamide, e.g., bis-ascrylylcystamine, which can be dissolved with 2-mecraptoethanol.

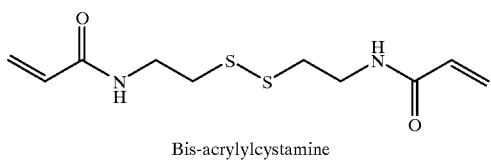

Bis-acrylylcystamine

Other useful cleavable monomer crosslinkers include, but are not limited to, N,N'-di-allyltartardiamide and N,N'-(1,2-dihydroxyethylene)bis-acrylamide.

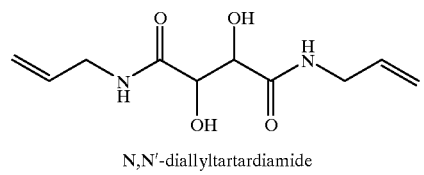

N,N'-diallyltartardiamide and

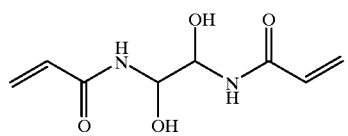

The subject compounds, dependent upon the particular molecule with which they are complementary, may be used by way of example as antagonists or agonists of hormones, receptors or enzymes; as modulators of gene expression, as antimicrobial compounds, as vaccines, as anti-tumor agents and as wound healing agents.

A preferred embodiment of the invention involves the production of compounds having a complementary structure to insulin. The resultant compounds will be advantageous to native insulin because they should be intrinsically more stable, i.e., more heat, enzymatically, and pH stable. Moreover, these compounds, given their pH stability, should be orally administrable. This is clearly a significant advantage as it may provide for the treatment of diabetes without the need for insulin injection.

Use of the subject compounds as in vivo therapeutic or prophylactic agents or in vivo diagnostic agents will generally entail the addition of a pharmaceutically acceptable carrier or excipient, e.g., water, phosphate buffered saline, surfactants, adjuvants, etc. Suitable carriers and excipients are well known to those skilled in the art.

The amount of the particular compound will depend upon factors including its activity, solubility, in vivo stability, and specific therapeutic or diagnostic application.

The subject compounds can be administered by any known means of administration, e.g., orally, intranasally, intravenously, intradermally, topically, subcutaneously, submuscularly, testicularly, rectally. Preferred means of administration include oral and intravenous injection.

A suitable dosage of the subject polymeric drug will generally range from about 0.00001 to 5.00 mg/kg of body weight, more preferably from about 0.01 to 1.00 mg/kg of body weight.

EXAMPLES

Example 1

This example describes the formation of a molecularly imprinted material using two differently reacting crosslinking monomers, A, and B. By virtue of choosing the mutual reactivity ratios (r) so that the product $r_A r_B < 1$, these monomers will preferably form stretches of homopolymers, rather than random, or alternating, copolymers. Polymerization of a mixture of these crosslinkers will lead to segment polymer formation: -A-A-A-A-B-B-B-B-A-A-A-A.

A solution comprising the two different crosslinkers, ethylene glycol dimethacrylate (EDMA) (FIG. 4, 23) and N1-((E)-1-(4-vinylphenyl)-methylidene)-4-vinylandine (VMVA) (FIG. 6, 2), together with the functional monomer methacrylic acid (MAA) (FIG. 4, 3), in acetonitrile is spraycoated onto the print molecule, immobilized onto a silicon wafer support (FIG. 3A). Upon exposure to UV-irradiation at 366 nm, polymerization takes place, during which a continuous three-dimensional segment polymer is formed around the print molecule (FIG. 3B). The thickness of this polymer can be controlled by the spraycoating process, and is normally in the range of 100 nm to 1 $\mu$m.

Treatment of the polymer with acidic/basic water solution for 24 hours leads to hydrolysis of the imine-bond of VMVA (FIG. 3C). This results in the dissolution of the VMVA-segments in the polymer, thus leading to the liberation of discrete polymer segment particles consisting mainly of EDMA and MAA. The size of the particles can be controlled by changing the ratio between EDMA and VMVA. In the ideal case, the particles are prepared in the nanometer range. Following extensive washing and removal of the polymer from the wafer support, these particles can be utilized in rebinding of the print molecule.

Example 2

This example demonstrates the use of two-dimensional movement in order to acquire anti-idiotype ligand formation.

A self-assembled monolayer (SAM), consisting of long-chain alkyl thiols (FIG. 9,1) is built on a gold surface (FIG. 5A). On top of this layer, a second layer is built, consisting of long-chain alcohols (FIG. 9,2) as well as crosslinkable, and functional alkenyl-structures (FIGS. 9,3–6)(FIG. 5B). In the second layer, the molecules are free to move within the layer in a random manner. Addition of a solution containing the target molecule, e.g., acetylcholine esterase (AChE), on top of the second layer, results in a directed arrangement of the functional alkenyl-molecules towards the enzyme. Patches of complexes between the functional alkenes and the enzyme takes place on the surface (FIG. 5C). These complexes are subsequently "frozen" by the addition of a crosslinker, such as tetramethyldisiloxane (TMDS)(FIG. 9,7)(FIG. 5D). After breakage of the layers, and removal of the enzyme, structures remain that are complementary to the active site of AChE (FIG. 5E). These polymer compounds may be used to affect acetylcholine esterate activity. Thus, these compounds, when combined with a pharmaceutically acceptable carrier or excipient are useful for treating conditions wherein modulation of acetylcholine esterase activity is therapeutically desirable.

Example 3

This example represents the use of molecular scaffolds to "freeze" a self-assembled complex between ligand building elements in their interaction with a binding site.

Crosslinked trypsin (from Altus), a proteolytic enzyme specific for the cleavage of peptide bonds (—X—Y—) where X can be any amino acid residue and Y is a positively charged residue, is mixed together with ligand building elements labeled with photoactive groups, e.g., perfluorophenylazido groups (FIGS. 10,1–2), chosen so as to be able to fit into the active site of the enzyme, and a preassembled scaffold-ligand element (FIG. 10,3) (FIG. 11A). The ligand elements, including the scaffold-bearing element, are prone to interact with the enzyme randomly. In order to enhance non-covalent interactions between the ligand building elements and the enzyme, and to reduce the amount of non-specific hydrophobic interactions, the process is performed in acetonitrile. After a period of time when self-assembly is allowed to be established (FIG. 11B), the solution is exposed to UV-radiation (254 nm) during which process the azido-functionalities will insert into the amino-functionalities of the scaffold. Finally, the active site-binding candidates are separated from the randomly binding adducts via affinity chromatography on a trypsin-column (FIG. 11C).

Example 4

This example describes a general method for the preparation of templated, linear, soluble polymers which display structural complementarity to the original molecule. (Serine protease.)

The serine protease trypsin (5 mg) is dissolved in aqueous sodium phosphate buffer (1 mL, pH 7, 0.05M). Alternatively, trypsin can be immobilized on an inert, insoluble support and then suspended in the aqueous sodium phosphate buffer. Acryloyl 4-aminobenzamidine (5 mg) (acryloyl 4-aminobenzamidine binds strongly to Asp 189 in the active site of trypsin), acrylamide (70 mg) and TEMED (6 $\mu$L) are added; additional functional monomers can also be introduced at this stage if desired. The mixture is equilibrated at room temperature for thirty minutes, degassed by purging with oxygen-free nitrogen and the polymerization initiated by the addition of 10% w/v ammonium persulphate in water (120 $\mu$L). Once the polymerization is complete (2–3 hours) the polymer is separated from the trypsin and unreacted monomers/initiator. This is achieved via a simple filtration step in the case of immobilized trypsin, or by passage of the reaction products through an affinity separation column which is specific for trypsin in the case of non-immobilized trypsin. Thereafter the linear, soluble, templated polymeric products are purified via repeated precipitation from water into methanol, and characterized via NMR and FTIR spectroscopy. The inhibitory properties of the resultant purified linear, soluble polymeric compounds versus trypsin are then tested in a standard enzyme assay.

Example 5

This example describes a general method for the preparation of templated, linear, soluble polymers which display structural complementarity to a print molecule, and which are obtained via the solubilization of insoluble, imprinted cross-linked polymers containing reversible, cleavable cross-linking moieties.

The serine protease trypsin (5 mg) is dissolved in aqueous sodium phosphate buffer (1 mL, pH 7, 0.05M). N-Acryloyl 4-aminobenzamidine (5 mg) (acryloyl 4-aminobenzamidine binds strongly to Asp 189 in the active site of trypsin), acrylamide (70 mg), N,N'-diallytartardiamide (5 mg) and TEMED (6 $\mu$L) are added; additional functional monomers can also be introduced at this stage if desired. The mixture is equilibrated at room temperature, degassed by purging with oxygen-free nitrogen and the polymerization initiated by the addition of 10% w/v ammonium persulphate in water (120 $\mu$L). Once the polymerization is complete (2–3 hours), the trypsin and unreacted monomers/initiator are removed by washing from the cross-linked polymer network using 10% v/v acetic acid in water containing 10% w/v SDS (5×10 mL); and the polymer then washed thoroughly with distilled water (5×10 mL) to remove traces of SDS and acetic acid. The cross-linked gel is then treated overnight with 2% w/v aqueous periodic acid (5 mL), the linear soluble, templated polymer isolated and purified via repeated precipitation using methanol. The polymer is characterized via NMR and FTIR spectroscopy and the inhibitory properties thereof versus trypsin tested via a standard enzyme assay.

Example 6

This example provides a lithographic method for the preparation of templated polymers which are complementary to the print molecules (e.g. proteins and cells) in terms of their surface relief and/or chemical structure (FIG. 7).

A silicon wafer is aminopropylated and insulin immobilized on the surface via a literature method (*Biochemistry*, Vol. 11:2291 (1972)). A solution of poly(methacrylic acid-co-glycidyl methacrylate) and the photoacid catalyst generator p-nitrobenzyl-9,10-dimethoxyanthracene-2-sulphonate in 2-methoxyethanol is then spin-coated onto the surface to the desired thickness (typically 1 μm), together with additional functional monomers and/or pre-polymers if desired. A photomask is put in place and the film exposed to filtered EM radiation from a super high-pressure mercury lamp (365 nm) for a set period of time (see *J. Appl. Polym. Sci.*, Vol. 50:243 (1993)). Following development of the film via treatment with aqueous tetramethylammonium hydroxide (2% w/v) followed by a post-exposure bake at elevated temperature (80° C.), the discrete imprinted particles are released from the silicon surface.

Example 7

This example provides a means for preparing linear, templated polymers which bind specifically to integrins, which are cell-surface based proteins that are involved in cell-cell or cell-matrix interactions in biological processes.

The integrin $\alpha_{IIb}\beta_3$ (1 mg), N-acryloyl L-arginine (5 mg), N-acryloyl L-glutamic acid (5 mg), acrylamide (50 mg) and TENED (5 μL) are suspended in aqueous sodium phosphate buffer (1 mL, pH 7). The mixture is equilibrated at room temperature, degassed by purging with oxygen-free nitrogen and polymerization initiated by the addition of 10% w/v ammonium persulphate in water (100 μL). After four hours the templated polymer is released from the integrin via the addition of the competing synthetic tripeptide RGD (100 mg) and the polymer isolated via fractional precipitation with saturated ammonium sulphate. The polymer is then purified via repeated precipitation from water into methanol.

Example 8

This method describes the synthesis of a polymeric inhibitor of α-chymotrypsin by direct molding of the polymer on the active site of such enzyme (FIG. 12).

Bovine α-Chymotrypsin can interact with iminodiacetic acid-Cu(II) complexes via its His-40 (Berna et al., *Biochemistry*, Vol. 36:6896 (1997)). Allyl-2-hydroxy-3(N, N-dicaboxymethylamino)propylether-Cu(II)(Baek,Haupt, Colin and Vijayalakshmi, *Electrophoresis*, Vol. 17:489 (1996)) is used as the anchoring monomer. Methacrylamide and methacrylic acid are used as the filling monomers.

Crosslinked crystalline α-Chymotrypsin (Altus) (240 mg) is mixed with 1 ml of a heptane solution containing allyl-2-hydroxy-3(N, N-dicarboxymethylamino)propylether Cu(II) (12.4 mg), methacrylamide (17 mg), methacrylic acid (17 mg) and 2,2'-azo-bis-isobutyronitrile (17.5 mg) in a 1.5 ml polypropylene test tube. After filling the head space of the tube with argon, the tube is cooled on ice. Polymerization is initiated by UV irradiation at 366 nm for 30 min. The suspension is filtered and the chymotrypsin crystals are washed four times with 1 M acetic acid in heptane. The filtrates are combined and the solvent is evaporated under vacuum. The remaining polymer is redissolved in 25 mM MOPS buffer pH 7 containing 0.3 M NaCl, and the solution is centrifuged. The supernatant is purified by affinity chromatography on a column containing His-Sepharose (Sigma), pre-equilibrated with 25 mM MOPS buffer pH 7 containing 0.3 M NaCl. The non-retained fraction is discarded, and elution is performed with 0.1 M sodium acetate buffer pH 4. The eluted polymer fraction is dialyzed overnight against 50 mM sodium phosphate buffer pH 7. The resulting polymer fraction containing metal chelate groups can be further fractionated by affinity chromatography on α-chymotrypsin immobilized onto agarose beads (Sigma). The retained polymer molecules are eluted with 50 mM sodium acetate buffer pH 4, containing 1 M NaCl. The eluted fraction is dialyzed against ultrapure water and freeze-dried. The polymer fractions are tested for their inhibitory effect versus α-chymotrypsin in a standard activity assay using BTEE.

Example 9

This example describes the synthesis of a polymeric competitor for antibody binding to its antigen by direct moulding of the polymer on the antibody's binding site.

Antibodies are immobilized onto porous silica beads. Polymerization takes place only in the pores of the beads which are suspended in a perfluorocarbon solution to prevent the polymerization mixture from exiting the pores. Monoclonal antibodies against lysozyme are used as model system and the resulting polymer specifically inhibits antigen binding to the antibody.

2 g of aminopropyl silica beads (10 μm diameter, average pore diameter of 100 Å) is suspended in 5 ml of a solution of 1 M succinic anhydride in THF. The suspension is sonicated for 30 min and subsequently incubated on a overhead shaker for 5 h at room temperature. The beads are removed by centrifugation and washed by incubation for 1 h each time with THF (2 times) and methanol (3 times) followed by centrifugation. The solvent is removed under vacuum. The beads are then suspended in 5 nil of a solution of 0.2 M EDC, 0.2 M NHS and 0.2 M methylmorpholine in THF and allowed to react overnight at room temperature on a overhead shaker. The beads are removed by centrifuigation and washed by incubation for 1 h each time with THF (2 times) and methanol (3 times) followed by centrifugation. The solvent is removed under vacuum.

The beads are packed in a FPLC column (10×0.5 cm) and washed with 50 mM phosphate buffer pH 7.5, 0.02% Tween-20, for 2 h at a flow rate of 1 ml/min. All following steps are carried out at 4° C. 5 ml of a solution of a sheep monoclonal antibody (IgG) against lysozyme (1 mg/ml in 50 mM phosphate buffer pH 7.5, 0.02% Tween-20) is repeatedly (3×) injected into the column at a flow rate of 0.2 ml/min. The column is then washed with phosphate buffer pH 7.5, for 2 h at a flow rate of 0.5 ml/min. The column is wrapped in aluminum foil and a solution containing methacrylic acid (10 mM), methacrylamide (20 mM, 1-vinylimidazole (10 mM and riboflavin (1 mM) in 50 mM phosphate buffer pH 7.5, is pumped through the column for 30 min at a flow rate of 0.2 ml/min. Perfluorocyclohexane is pumped through the column at a flow rate of 1 ml/min. When all buffer contained in the interstitial pores of the column has been eliminated, the column is illuminated for 2 h under a fluorescent tube light source. 10 mM phosphate buffer pH 7.5 is pumped through the column at a flow rate of 1 ml/min and the effluent collected. The buffer phase containing the polymer is separated from the perfluorocyclohexane phase and freeze-dried. The remainder is dissolved in 2 ml of 10 mM phosphate buffer pH 7.5, 0.02% Tween-20, and chromatographed on a Sephadex G-5 gel filtration column to remove salts and unreacted monomers. The eluted polymer fraction is rechromatographed on the IgG-FPLC column, previously equilibrated with 10 mM phosphate buffer pH 7.5, 0.02% Tween-20. The retained polymer is eluted using a stepwise decreasing pH gradient (pH 7.5-3) followed by a solution of 200 mM formic acid in water, pH 3, containing 1 M NaCl. The eluted fractions are freeze-dried, redissolved in water and chromatographed on a Sephadex G-5 gel filtration column to remove salts. The ability of the polymer fractions to inhibit lysozyme binding to a sheep-anti-lysozyme monoclonal antibody (the same as used in the moulding step) is evaluated in a direct ELISA.

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

We claim:

1. A method for producing a compound suitable for in vitro or in vivo usage as a diagnostic, therapeutic, purification, separation, or prophylactic agent that possesses a complementary structure to a specific site on a target molecular entity or portion thereof by site-specific molecular imprinting comprising the following steps:
   (i) selecting a particular molecular entity to which a compound having a complementary structure is to be produced;
   (ii) contacting such molecular entity with one or more complementary monomers under conditions wherein such monomers associate around one or more residues of such molecular entity;
   (iii) effecting polymerization of such associated monomers optionally in the presence of at least one crosslinking agent to produce a polymeric coating on the surface of said molecular entity and which possesses a complementary structure to said biological entity or a portion thereof;
   (iv) removing said molecule under conditions that result in a polymeric compound that possesses a complementary structure to said molecular entity or portion thereof; and
   (v) optionally effecting one or more cleavage and/or dissociation steps to produce compounds that are suitable for in vivo or in vitro usage as a diagnostic, therapeutic, purification, separation and/or prophylactic agent.

2. The method of claim 1, wherein said molecule is immobilized to a support.

3. The method of claim 1, wherein said molecular entity and is selected from the group consisting of a protein, a nucleic acid sequence, a carbohydrate, a peptide, a glycoprotein, a cell, a virus, a pathogen, and a tissue.

4. The method of claim 3, wherein said protein is selected from the group consisting of an enzyme, antigen, antibody, hormone, receptor, and a fragment thereof.

5. The method of claim 1, wherein the crosslinking agent comprises at least one cleavable crosslinker.

6. The method of claim 5, wherein said crosslinker is selected from the group consisting of bis-acrylcystamine, N,N-diallyltartardiamide, N,N-(1,2-dihydroxyethylene) bisacrylamide, N,N'-bis-(acryloyl)cystamine, N1-(CE)-1-(4-vinylphenyl)methylidene)-4-vinyl aniline, allyl disulfide, and bis-(2-(methacryl, 1-oxyethyl)) disulfide.

7. A method of using the compound in vivo produced according to claim 1 as a therapeutic or diagnostic agent comprising administering to a subject in need of such treatment a therapeutically or diagnostically effective amount of said compound.

8. The method according to claim 1, wherein the molecule to which a compound having a complementary structure is to be produced is insoluble.

9. The method of claim 8, wherein said molecule is an enzyme crystal or a crosslinked enzyme.

10. An improved method of affinity purification which purifies a compound using a compound that specifically binds thereto, wherein the improvement comprises using a compound produced according to claim 1 to effect purification.

11. An improved assay method which includes a competitive affinity ligand wherein the improvement comprises using as the competitive affinity ligand a compound produced according to claim 1.

12. The method of claim 1, wherein the compound produced by said method is suitable for use as an active agent selected from the group consisting of a hormone, enzyme, receptor antagonist or agonist; gene expression modulator, antimicrobial agent, and an anti-tumor agent.

13. The method of claim 1, wherein the compound which results from said method is subsequently attached to a therapeutic or diagnostic agent.

14. A method for producing a polymeric compound that exhibits complementary structure to a specific site on a cell or virus by site specific molecular imprinting comprising the following steps:
   (i) optionally immobilizing said cell or virus to a support;
   (ii) coating said optionally immobilized cell or virus with a polymer that is crosslinkable under specific conditions;
   (iii) selectively crosslinking the portion of the coating that is proximate to the cell or virus; and
   (iv) removing the resultant molecular coating from the cell or virus.

15. The method of claim 14, wherein the polymer is a photocrosslinkable polymer.

16. The method of claim 15, wherein the polymer areas not proximate to the immobilized microbial or mammalian cell are covered with a photomask during photocrosslinking.

17. The method of claim 14, wherein the support is a thin layer support.

18. The method of claim 14, wherein the polymer coating in step (ii) is introduced by a method selected from the group consisting of spray-coating, dip-coating, and spin-coating.

19. The method of claim 14, wherein the resultant polymeric coating is suitable for use as a cell separating material.

20. The method of claim 14, wherein the molecular coating is subsequently cleaved into oligomers which function as anti-microbial agents.

21. A method for producing a compound that has a complementary structure to the active or binding site of a molecular entity by site-specific molecular imprinting comprising the following steps:
   (i) providing a support which is coated with a first monomer layer coating;
   (ii) applying to said first layer a second layer which comprises at least one crosslinkable monomer which is able to move freely in said second layer;
   (iii) exposing said second layer to a molecular entity containing at least one active or binding site and allowing for said crosslinkable monomer to associate around said at least one active site;
   (iv) providing a crosslinking agent and effecting crosslinking to produce a crosslinked compound that possesses a complementary structure to said at least one active or binding site; and
   (v) recovering said crosslinked compound that possesses a complementary structure to said at least one active or binding site or sites.

22. The method of claim 21, wherein said molecular entity is an enzyme or a receptor.

23. The method of claim 22, wherein the resultant compound functions as an antagonist or agonist.

24. A method for producing a polymeric compound that has a complementary structure to a specific site on a molecular entity by site-specific molecular imprinting which method comprises the following steps:
- (i) providing a preformed functionalized polymer that is linear or partially crosslinked and contacting same with a molecular entity such that specific functional groups on the polymer interact covalently or non-covalently with specific residues on the molecular entity;
- (ii) allowing for such non-covalent or covalent interactions between the functional groups on the polymer and the molecular entity to equilibrate;
- (iii) subjecting the resultant equilibrated covalent or non-covalent complex between the polymer and the molecular entity to at least one of the following steps:
    - (1) chemically treating the functional groups on the polymer that interact least strongly with the molecular entity by site-selective chemical modification;
    - (2) chemically treating the functional groups on the polymer that interact most strongly with the molecular entity by site-selective chemical modification; and/or
    - (3) crosslinking the polymer;
- (iv) separating the molecular entity from the resultant polymer.

25. The method of claim 24, wherein the molecular entity is in solution or immobilized to a support.

26. The method of claim 24, wherein crosslinking is effected using a reversible cleavable crosslinking agent.

27. A compound produced according to claim 1.

28. A compound produced according to claim 14.

29. A compound produced according to claim 21.

30. A compound produced according to claim 25.

31. The method of claim 1, wherein the resultant polymer ranges in molecular weight from about 1000 to about 200,000.

32. The method of claim 31, wherein the molecular weight ranges from about 5,000 to 50,000.

33. The method of claim 1, wherein the chain length of the resultant polymer ranges from about 25 to 2500 angstroms.

34. The method of claim 33, wherein the chain length ranges from 250 to 1000 angstroms.

35. A method for producing a compound suitable for in vitro or in vivo usage as a therapeutic agent that possesses a complementary structure to a specific site on a target molecule or portion thereof by site-specific molecular imprinting comprising the following steps:
- (i) selecting a particular molecule to which a compound having a complementary structure is to be produced;
- (ii) contacting such molecule with one or more complementary monomers under conditions wherein such monomers associate around one or more residues of such molecule;
- (iii) effecting polymerization of such associated monomers optionally in the presence of at least one crosslinking agent to produce a polymeric coating which possesses a complementary structure to said specific site of said molecule or a portion thereof;
- (iv) removing said molecule to produce a compound that possesses a complementary structure to said specific site of said molecule or portion thereof; and
- (v) optionally effecting one or more cleavage and/or dissociation steps to produce a compound that is suitable for in vivo usage as a therapeutic agent.

36. The method of claim 35, wherein said specific site constitutes an active or specific binding site.

37. The method of claim 1, wherein said polymeric compound is an oligomeric compound.

38. The method of claim 24, wherein said polymeric compound is an oligomeric compound.

* * * * *